US008530638B2

(12) United States Patent
Bulyk et al.

(10) Patent No.: US 8,530,638 B2
(45) Date of Patent: Sep. 10, 2013

(54) SPACE EFFICIENT POLYMER SETS

(75) Inventors: Martha L. Bulyk, Weston, MA (US);
Anthony A. Philippakis, Cambridge, MA (US); Preston Wayne Estep, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 189 days.

(21) Appl. No.: 12/824,983

(22) Filed: Jun. 28, 2010

(65) Prior Publication Data

US 2010/0267572 A1    Oct. 21, 2010

Related U.S. Application Data

(63) Continuation of application No. 11/112,349, filed on Apr. 22, 2005, now abandoned.

(60) Provisional application No. 60/587,066, filed on Jul. 12, 2004, provisional application No. 60/564,864, filed on Apr. 23, 2004.

(51) Int. Cl.
*C12Q 1/68* (2006.01)
*C07H 21/02* (2006.01)

(52) U.S. Cl.
USPC .......................... 536/24.3; 536/23.1; 435/6.1

(58) Field of Classification Search
None
See application file for complete search history.

(56) References Cited

U.S. PATENT DOCUMENTS

| | | |
|---|---|---|
| 6,326,489 B1 | 12/2001 | Church et al. |
| 6,410,243 B1 | 6/2002 | Wyrick et al. |
| 6,544,745 B2 | 4/2003 | Davis et al. |
| 6,548,021 B1 | 4/2003 | Church et al. |
| 2001/0053519 A1 | 12/2001 | Fodor et al. |
| 2002/0025531 A1 | 2/2002 | Suyama et al. |
| 2002/0058252 A1 | 5/2002 | Ananiev et al. |
| 2002/0177218 A1 | 11/2002 | Fang et al. |

FOREIGN PATENT DOCUMENTS

| | | |
|---|---|---|
| WO | WO 98/53059 | 11/1998 |
| WO | WO 02/18648 | 3/2002 |

OTHER PUBLICATIONS

Reid T. et al. Cancer Research 54, 1801-1806, Apr. 1, 1994.*
Liu Z. et al. BMC Genomics 2008, 9:509, pp. 1-17.*
Adams, M. et al. "The genome sequence of *Drosophila melanogaster*," Science 287, 2185-2195 (2000).
Beer, M.A. & Tavazoie, S. "Predicting gene expression from sequence," Cell 117, 185-98 (2004).
Benos, P., Bulyk, M. & Stormo, G. "Additivity in protein-DNA interactions: how good an approximation is it?," Nucleic Acids Res. 30, 4442-4451 (2002).
Bulyk ML, Gentalen E, Lockhart DJ, Church GM. Quantifying DNA-protein interactions by double-stranded DNA arrays. Nature Biotechnology (1999) 17(6):573-7.
Bulyk ML, Huang XH, Choo Y, Church GM. Exploring the DNA binding specificities of zinc fingers with DNA microarrays. Proc Natl Acad Sci USA (2001) 98(13):7158-7163.
Bulyk, M., Johnson, P. & Church, G. "Nucleotides of transcription factor binding sites exert interdependent effects on the binding affinities of transcription factors, " Nucleic Acids Res. 30, 1255-1261 (2002).
Cleveland, W. & Devlin, S. "Locally weighted regression: An approach to regression analysis by local fitting," *J. American Statistical Association* 83, 596-610 (1988).
Cliften, P. et al. "Finding functional features in *Saccharomyces* genomes by phylogenetic footprinting.," Science 301, 71-76 (2003).
DeRisi, J.K., Iyer, V.R. & Brown. P.O. "Exploring the metabolic and genetic control of gene expression on a genomic scale," Science 278, 680-686 (1997).
Desjarlais, J.R. & Berg, J.M. "Toward rules relating zinc finger protein sequences and DNA binding site preferences.," Proc. Natl. Acad. Sci. USA 89, 7345-7349 (1992).
Difley, J. & Stillman, B. "Purification of a yeast protein that binds to origis of DNA replication and a transcriptional silencer, " Proc. Natl. Acad. Sci. USA 85, 2120-2124 (1988).
Doi N, Takashima H, Kinjo M, Sakata K, Kawahashi Y, Oishi Y, Oyama R, Miyamoto-Sato E, Sawasaki T, Endo Y, Yanagawa H. Genome Research (2002) 12(3):487-92.
Dudley, A., Aach, J., Steffen, M. & Church, G. "Measuring absolute expression with microarrays with a calibrated reference sample and an extended signal intensity range, " Proc. Natl. Acad. Sci. USA 99, 7554-7559 (2002).
Email from Oxford Journals Regarding Publication Date for Patent Purposes of Kwan et al. (2003), Nov. 23, 2007, p. 1.
Gasch, A.P. et al. "Genomic expression programs in the response of yeast cells to environmental changes," Mol. Biol. Cell 11, 4241-57 (2000).
Hartemink, A., Gifford, D., Jaakkola, T. & Young, R. "Combining location and expression data for principled discovery of genetic regulatory network models," Pac. Symp. Biocomput., 437-449 (2002).
Ho, Y et al. "Systematic identification of protein complexes in *Saccharomyces cerevisiae* by mass spectrometry," Nature 415, 180-183 (2002).
Hughes, J.D., Estep, P.W., Tavazoie, S. & Church, G.M. "Computational identification of cis-regulatory elements associated with groups of functionally related genes in *Saccharomyces cerevisiae*," *J. Mol. Biol.* 296, 1205-1214 (2000).
Hughes, T.R. et al. "Functional discovery via a compendium of expression profiles," Cell 102, 109-26 (2000).
Ihaka, R. & Gentleman, R. "R: A language for data analysis and graphics," *J. Computational and Graphical Statistics* 5, 299-314 (1996).
Ito, T. et al. "Toward a protein-protein interaction map of the budding yeast: A comprehensive system to examine two-hybrid interactions in all possible combinations between the yeast proteins," Proc. Natl. Acad. Sci. USA 97, 1143-1147 (2000).
Iyer, V.R. et al. "Genomic biding sites of the yeast cell-cycle transcription factors SBF and MBF," Nature 409, 533-538 (2001).

(Continued)

*Primary Examiner* — Stephen Kapushoc
(74) *Attorney, Agent, or Firm* — Fish & Richardson P.C.

(57) ABSTRACT

The disclosure features a collection that comprises a plurality of polymers, typically nucleic acid molecules in a compact form. The molecules include all possible sequences or at least a certain percentage of all possible sequences, of a particular length.

9 Claims, No Drawings

(56) References Cited

OTHER PUBLICATIONS

Jiang, R. & Carlson, M. "The Snf1 protein kinase and its activating subunit, Snf4, interact with distinct domains of the Sip1/Sip2/Gal83 component in the kinase complex," *Mol. Cell. Biol.* 17, 2099-106 (1997).

Kellis, M., Patterson, N., Endrizzi, M., Birren, B. & Lander, E. "Sequencing and comparison of yeast species to identify genes and regulatory elements," *Nature* 423, 241-254 (2003).

Konig, P., Giraldo, R., Chapman, L. & Rhodes, D. "The crystal structure of the DNA-binding domain of yeast RAP1 in complex with telomeric DNA." *Cell* 85, 125-136 (1996).

Krylov et al. (2001) Nucleic Acids Research 29:2654-2660 (2001).

Kwan AH, Czolij R, Mackay JP, Crossley M. Pentaprobe: a comprehensive sequence for the one-step detection of DNA-binding activities. Nucleic Acids Research (2003) 31(20):e124.

Lander, E.S. et al. "Initial Sequencing and analysis of the human genome," *Nature* 409, 860-921 (2001).

Lee, M.I., Bulyk, M., Whitmore, G. & Church, G. "A statistical model for investigating binding probabilities of DNA nucleotide sequence using microarrays," *Biometrics* 58, 981-988 (2002).

Lee, T. et al. "Transcriptional regulatory networks in *Saccharomyces cerevisiae*," *Science* 298, 799-804 (2002).

Lieb, J.D., Liu, X., Botstein, D. & Brown, P.O. "Promoter-specific binding of Rap 1 revealed by genome-wide maps of protein-DNA association," *Nat. Genet.* 28, 327-334 (2001).

Liu, X., Brutlag, D. & Liu, J. "BioProspector: discovering conserved DNA motifs in upstream regulatory regions of co-expressed genes," *Pac. Symp. Biocomput.*, 6, 127-138 (2001).

Lutfiyya, L.L. et al. "Characterization of three related glucose repressors and genes they regulate in *Saccharomyces cerevisia*," *Genetics* 150, 1377-1391 (1998).

Man, T.K. & Stormo, G.D. "Non-independence of Mnt repressor-operator interaction determined by a new quantitative multiple fluorescence relative affinity (QuMFRA) assay." *Nucleic Acids Res.* 29, 2471-2478 (2001).

McBroom, L.D. & Sandowski, P.D. "DNA bending by *Saccharomyces cerevisiae* ABFI and its proteolytic fragments," *J. Biol. Chem.* 269, 16461-16468 (1994).

Mukherjee s. et al. Rapid analysis of the DNA-binding specificities of transcription factors with DNA microarrays. Nature Genetics (2004) 36(12):1331-1339.

Oliphant, A.R., Brandl, C.J. & Struhl, K. "Defining the sequence specificity of DNA-binding proteins by selecting binding sites from random-sequence oligonucleotides: analysis of yeast GCN4 protein," *Mol. Cell. Biol.* 9, 2944-2949 (1989).

Palecek, S.P., Parikh, A.S., Huh, J.H. & Kron, S.J. "Depression of *Saccharomyces cerevisiae* invasive growth on non-glucose carbon sources requires the Snf1 kinase," *Mol. Microbiol.* 45, 453-69 (2002).

Planta, R.J. "Regulation of ribosome synthesis in yeast," *Yeast* 13, 1505-18 (1997).

Rae, F.K. et al. "Analysis of complementary expression profiles following WT1 induction versus repression reveals the cholesterol/fatty acid synthetic pathways as a possible major target of WT1," *Oncogene* 23, 3067-79 (2004).

Ren, B. et al. "Genome-wide location and function of DNA binding proteins." *Science* 290, 2306-2309 (2000).

Robinson, M., Grigull, J., Mohammad, N. & Hughes, T. "FunSpec: a web-based cluster interpreter for yeast," *BMC Bioinformatics* 3, 35 (2002).

Robinson. K., McGuire, A.M. & Church, G.M. "A comprehensive library of DNA-binding site matrices for 55 proteins applied to the complete *Escherichia coli* K-12 genome," *J. Mol. Biol.* 284, 241-254 (1998).

Roulet E. et al., "High-Throughput Selex Sage Method for quantitative Modeling of Transcription-Factor Binding Sites," Nat. Biotechnol., Aug. 2002, 20(8):831-5.

Schena, M., Shalon, D., Davis, R.W. & Brown, P.O. "Quantitative monitoring of gene expression patterns with a complimentary DNA microarray," *Science* 270, 467-470 (1995).

Schneider, T.D. & Stephens, R.M. "Sequence logos: a new way to display consensus sequences," *Nucleic Acids Res.* 18, 6097-100 (1990).

Sokal, R. & Rohlf, R. *Biometry: The Principles and Practice of Statistics in Biological Research*, (W.H. Freeman and Company, New York 1995).

Stuart, J.M., Segal, E., Koller, D. & Kim, S.K. "A gene-coexpression network for global discovery of conserved genetic modules," *Science* 302, 249-55 (2003).

Tavazoie, S., Hughes, J., Campbell, M., Cho, R. & Church, G. "Systematic determination of genetic network architecture," *Nat. Genet.* 22, 281-285 (1999).

Tuerk C, Gold L. Systematic evolution of ligands by exponential enrichment: RNA ligands to bacteriophage T4 DNA polymerase. Science (1990) 249(4968):505-510.

Udalova, I., Mott, R., Field, D. & Kwiatkowski, D. "Quantitative prediction of NF-kappa B DNA-protein interactions," *Proc. Natl. Acad. Sci. USA* 99, 8167-8172 (2002).

Uetz, P. et al. "A comprehensive analysis of protein-protein interactions in *Saccharomyces cerevisiae*," *Nature* 403, 623-627 (2000).

Unnikrishnan, I., Miller, S., Meinke, M. & LaPorte, D.C. "Multiple positive and negative elements involved in the regulation of expression of *GSY1* in *Saccharomyces cerevisiae*," *J Biol. Chem* 278, 26450-7 (2003).

Venter, J.C. et al. "The sequence of the human genome," *Science* 291, 1304-1351 (2001).

Wingender, E. et al. "TRANSFAC: an integrated system for gene expression regulation," *Nucleic Acids Res.* 28, 316-319 (2000).

Wodicka, L., Dong, H., Mittmann, M., Ho, M.H. & Lockhart, D.J. "Genome-wide expression monitoring in *Saccharomyces cerevisiae*," *Nat. Biotechnol.* 15, 1359-1367 (1997).

Zawel L. et al., "Human Smad3 and Smad4 Are Sequence-Specific Transcription Activators' Molecular Cell," Mar. 1998, vol. 1, pp. 611-617.

Zhu, H. et al. "Global analysis of protein activities using proteome chips," *Science* 293, 2101-2105 (2001).

Office Action, in U.S. Appl. No. 11/112,349, mailed Jun. 26, 2007.
Reply to Office Action, in U.S. Appl. No. 11/112,349, filed Aug. 27, 2007.
Office Action, in U.S. Appl. No. 11/112,349, mailed Nov. 30, 2007.
Reply to Office Action, in U.S. Appl. No. 11/112,349, mailed May 30, 2008.
Office Action, in U.S. Appl. No. 11/112,349, mailed Sep. 16, 2008.
Reply to Office Action, in U.S. Appl. No. 11/112,349, filed Feb. 13, 2009.
Office Action, in U.S. Appl. No. 11/112,349, mailed Jul. 9, 2009.
Reply to Office Action, in U.S. Appl. No. 11/112,349, filed Dec. 9, 2009.
Office Action, in U.S. Appl. No. 11/112,349, Mar. 8, 2010.

\* cited by examiner

SPACE EFFICIENT POLYMER SETS

CROSS-REFERENCE TO RELATED APPLICATIONS

This application is a continuation of U.S. application Ser. No. 11/112,349, filed on Apr. 22, 2005, which claims priority to provisional application Ser. Nos. 60/564,864, filed on Apr. 23, 2004, and 60/587,066, filed on Jul. 12, 2004, the contents of which are incorporated by reference in their entireties.

BACKGROUND

Nucleic acid arrays have a variety of uses. One application enables evaluating the binding specificity of nucleic acid binding proteins.

SUMMARY

In one aspect, the disclosure features a collection that comprises a plurality of nucleic acid molecules. The molecules include all possible sequences or at least a certain percentage (e.g., at least 10, 25, 50, 60, 70, 80, 90, 95, 98, 99, 99.9%) of all possible sequences, of a particular length, k. These sequences are termed "k-mers." k can be, for example, greater or equal to 5, 6, 7, 8, 9, 10, or 12 or, e.g., between 6-20, 6-18, 8-15, or 8-12. Each molecule of the plurality has length greater than k, e.g., a length of k+n nucleotides. For example, n is at least 1, 2, 3, 5, or 10. Typically, the nucleic acid molecules of the plurality are substantially longer than k, and can be at least 1.5×k nucleotides long or at least an integral multiple of k, e.g., at least 2×k nucleotides long, further examples of multiples include at least 2.2, 2.5, 2.7, 3.0, 3.2, 3.5, 4, 4.5, 5, 6, 7, and ranges in between. In one embodiment, at least some molecules of the plurality (and typically all molecules of the plurality) include at least two, three, four, or five different k-mers.

In one embodiment, the number of unique nucleic acid molecules of the plurality is fewer than the number of all possible k-mer sequences or, if the collection includes only a certain percentage of such sites, fewer than the number of such sequences. The compaction ratio (defined as the number of unique molecules divided by the number of represented k-mers) can be, for example, less than 0.5, 0.2, 0.1, 0.06, 0.05, 0.01, or 0.002. Thus, in an embodiment in which all possible sites of length k are represented, the collection includes fewer molecules than the number of all such possible sequences. This compact design is achieved by including more than one k-mer per molecule, while maintaining similar k-mers at different molecules of the collection.

The nucleic acid molecules of the collection can be in solution, can be labeled, can be present in separate containers, in pools, or can be immobilized, e.g., on one or more beads or on an array. The nucleic acid molecules can each also include an invariant region, e.g., a primer binding site and/or a spacer sequence.

In one embodiment, the nucleic acid molecules of the plurality are all less than 150 nucleotides in length, e.g., less than 120, 100, 80, 75, 70, 65, or 60. For example, the nucleic acid molecules of the plurality can be between 30-75 or 50-70 nucleotides in length. In one embodiment, at least 1, 2, 5 or 10% of the molecules of the plurality include artificial sequences or sequences not present in a yeast intergenic region.

In another aspect, the disclosure features a collection that comprises a plurality of non-homogeneous polymer molecules. The molecules include all possible sequences or at least a certain percentage (e.g., at least 10, 25, 50, 60, 70, 80, 90, 95, 98, 99, 99.9%) of all possible sequences, of a particular length, k. These sequences are termed "k-mers." k can be, for example, greater or equal to 5, 6, 8, 10, or 12 or, e.g., between 6-20, 6-18, 8-15, or 8-12. Each molecule of the plurality may have the same length, or the lengths may vary. For example, most of the molecules of the collection can have a length of at least k+n subunits. n can be at least 1, 2, 3, 5, or 10. Typically, most of the molecules of the collection are substantially longer than k, e.g., at least 2×k subunits long. In one embodiment, at least some molecules of the plurality (and typically all molecules of the plurality) include at least two, three, four, or five different k-mers.

In one embodiment, the polymer includes a nucleic acid backbone, a peptide backbone, or a sugar backbone. For example, the polymer can be a polypeptide (e.g., a peptide of between 3-30 amino acids) or a larger polypeptide (e.g., greater than 30 amino acids). In embodiments in which the polymer is a nucleic acid, the nucleic acid can be RNA, DNA, or a combination thereof It can be double-stranded, partially double-stranded, or single-stranded. For example, partially double-stranded and single-stranded molecules may include tertiary structures, e.g., hairpins, bulges and so forth. In a preferred embodiment, at least the variant region of molecules, e.g., the region that includes the different k-mers, in the collection is double-stranded.

In one embodiment, the number of unique nucleic acid molecules of the plurality is fewer than the number of all possible sites or, if the collection includes only a certain percentage of such k-mer sequences, fewer than the number of such sequences. The compaction ratio (defined as the number of unique molecules divided by the number of represented k-mers) can be, for example, less than 0.5, 0.2, 0.1, 0.05, 0.01, or 0.002. Thus, in an embodiment in which all possible sites of length k are represented, the collection includes fewer molecules than the number of all such possible sequences. This compact design can be achieved by including more than one different k-mer per molecule, and by locating similar k-mers (e.g., k-mers that differ by only one or two nucleotides) in different molecules of the collection.

The molecules of the collection can be in solution, can be labeled, can be present in separate containers, in pools, or can be immobilized, e.g., on one or more beads or on an array, in cells, or attached to or contained in viruses. The collection can be used to evaluate an interaction between a molecule of interest and members of the collection.

In another aspect, the disclosure features a nucleic acid array that includes all possible sites or at least a certain percentage (e.g., at least 10, 25, 50, 60, 70, 80, 90, 95, 98, 99, 99.9%) of all possible sites, of a particular length, k. These sites are termed "k-mers." k can be, for example, greater or equal to 5, 6, 8, 10, or 12 or, e.g., between 6-20, 6-18, 8-15, or 8-12. The array includes a plurality of addresses. Most addresses of the plurality includes at least one nucleic acid molecule of length greater than k and the molecules at each address of the plurality may have the same length, or the lengths may vary. In certain embodiments, most of the nucleic acid molecules of the collection are at least k+n nucleotides long. For example, n is at least 1, 2, 3, 5, or 10. Typically, most of the nucleic acid molecules of the collection are substantially longer than k, and in preferred embodiments most of the nucleic acid molecules of the collection are at least 2×k nucleotides long.

In one embodiment, the number of unique nucleic acid molecules physically associated with the array is fewer than the number of all possible sites or, if the array includes only a certain percentage of such sites, fewer than the number of such sites. The compaction ratio (defined as the number of unique molecules divided by the number of represented k-mers) can be, for example, less than 0.5, 0.2, 0.1, 0.05, 0.01, or 0.002. Thus, in a typical embodiment, even though all possible sites of length k are represented, the array can have fewer unique addresses than the number of all such possible sites. This compact design is achieved by including more than one k-mer per address, while maintaining similar k-mers at different addresses.

One method for producing a collection of nucleic acids described herein includes representing the collection as a string or a small number of strings. The Hamming distance function or any other distance function can be used to define sequence similarity among k-mers. Related sequences that are seen to be located in a common region of theoretical sequence space (e.g., a "Hamming ball") are arranged in the string, and, hence, in the array, so that they are discernable (e.g., distributed to different addresses) from each other and recoverable. This design enables fine discrimination for evaluating specificity. Other exemplary distance functions include: a Euclidean distance, z-score distance, Bhattacharya distance, Mahalanobis distance, Matusita distance, divergence metric, Chernoff distance, angular metric, Earth Mover's distance, Hausdorff distance, City Block (Manhattan) distance, Chebychev distance, Minkowski distance, or Canberra distance.

One method for using a collection of nucleic acid molecules described herein is to evaluate a molecule of interest (e.g., a protein, a drug, a nucleic acid aptamer), a sample, or a functional event (e.g., as a bio-sensor). In one embodiment, a collection of nucleic acid molecules in an array is to evaluate the specificity of a nucleic acid binding compound, e.g., a nucleic acid binding protein, e.g., a DNA binding protein, such as a transcription factor or an enzyme (e.g., a methylase or restriction endonuclease, etc). In some cases, a protein or nucleic acid can be modified. For example, protein modifications include phosphorylation, ubiquitination, acetylation, and methylation. These modifications are typically site specific. The protein or nucleic acid can also be present in a complex, e.g., with other macromolecules. For example, a protein complex that includes at least two or three polypeptide chains can be used. All the polypeptide chains can differ or, e.g., as in a complex that includes a homodimer, some chains can be the same.

Interactions between a compound of interest with addresses of the array are evaluated, and the interaction data is processed to identify one or more sites with which the protein interacts. For example, if each possible k-mer is present at plurality of addresses, it is possible to deconvolve the interaction data to identify one or more k-mers that interact with the compound.

In one embodiment, the collection of nucleic acid molecules is used to identify a nucleic acid of interest, e.g., an aptamer with binding or enzymatic activity, e.g., with respect to a target protein, e.g., an enzyme or cell-surface protein. For example, the protein can be associated with a disease or disorder. A nucleic acid molecule that binds to and/or inhibits the target protein can be used, e.g., to detect or modulate the disease or disorder.

In another embodiment, the collection of nucleic acid molecules is used to characterize a sample (e.g., a complex sample, e.g. a sample obtained from a subject, e.g., a patient). The pattern of interaction can be used to identify or characterize the sample.

Accordingly, in one embodiment, the collection of nucleic acid molecules can be used to characterize the binding preferences of nucleic acid binding molecules. Since all possible DNA sequence variants can be represented on DNA microarrays in a space- and cost-efficient manner, a reduced number of individual DNA sequences and individual DNA spots can be synthesized. This reduction also can have implications on the density and/or number of addresses on synthesized microarrays.

Since the nucleic acid molecules are longer (e.g., significantly longer) than k so that the addition of each base to the length of an oligonucleotide ("oligo") adds another k-mer to that oligonucleotide. For example, considering 10-mers (e.g., DNA sites 10 nucleotides long), a fifty base long oligo would contain 41 distinct 10-mers, and a sixty base oligo would contain 51 distinct 10-mers. Compared to the use of a single k-mer per oligo, this approach can greatly reduce the number of molecules required to characterize the binding, enzymatic, or other physical or functional interactions.

In one embodiment, the nucleic acid includes k-mers, where k is greater than 5, 6, 7, or 8, e.g., a biologically relevant size, and every k-mer or at least the certain percentage of such k-mers, is represented in at least two different nucleic acid molecules.

In one embodiment, in which the nucleic acids of the collection are immobilized on a surface, those two different nucleic acid molecules for a particular k-mer would be located at distinguishable addresses. Each k-mer in the collection can represented at least once, twice, or more (e.g., 3, 4, or 5) times with a variety of flanking bases (e.g., in different nucleic acid molecules). The flanking bases could be either a particular sequence (e.g., non-degenerate) or be degenerate (e.g., N which is a mixture of A, C, G, and T, or R which is a mixture of G and A). The form of this collection of k-mers could be variable. For example, in one embodiment, the collection is provided as an array, e.g., an array of double-stranded oligonucleotides. The oligonucleotides can be, for example, in the range of 10 to 100 bases.

In one embodiment, each k-mer of the collection can be flanked by each of the four nucleotides on both sides, resulting in sixteen variants. For example, considering ACGT, it would be most informative to have AACGTA, AACGTC, AACGTG, AACGTT, CACGTA, CACGTC, CACGTG, CACGTT, GACGTA, GACGTC, GACGTG, GACGTT, TACGTA, TACGTC, TACGTG, and TACGTT represented on a DNA microarray.

If not every k-mer is present in a collection, it is possible, for example, that the omitted k-mers have particular qualities, e.g., homo-polymeric sequences or sequences that include only two different types of nucleotides, and so forth. In certain embodiments, most k-mers are represented within the collection more than once. In preferred embodiments the sequence of a given k-mer is represented within a given molecule shared with other k-mers, and the sequence of this given k-mer is present on at least a second molecule wherein few or none of the other k-mers present on the given first molecule are present on the second molecule. While wishing not to be bound by theory, it is understood that multiple representations of a given k-mer can allow a more precise assignment of which k-mer of a molecule is being bound or otherwise subject to an interaction, and restricting, reducing, or eliminating, occurrences of pairs of k-mers to single occurrences allows more precise determinations of which k-mer within a molecule is being bound or subject to an interaction.

In certain embodiments, to allow the binding site specificity of a DNA binding molecule to be determined completely and readily from a collection of DNA sequences, it is possible to design of such DNA sequences with one or more of the following exemplary features: a) for example, requiring all possible DNA binding sites within a given binding space (termed a 'Hamming ball' (a 'Hamming ball' refers to a particular k-mer and the k-mers that are within an arbitrary number of mismatches from it) to be located on separate molecules in the collection); b) for example, requiring multiple copies of a given k-mer, with each copy flanked by unique flanking sequence so as to take into account potential junction effects; c) for example, requiring that a given k-mer, if it is located at one end of one molecule, then it should preferably be located either centrally within or at the other end of another molecule (e.g., to account for possible steric effects, surface attachment, synthesis, and/or the requirement for flanking DNA sequence); 4) designing molecules of the collection such that k-mers within a given Hamming ball might be found on either strand (forward or reverse complement), if double-stranded molecules are used.

There are a number of possible ways to design such a set of DNA sequences. In one embodiment, we have calculated what we believe to be is a maximally compact representation of all possible binding sites. For this approach, we addresses requirements for generating one string that contains every k-mer exactly once, when considering words in a stacked fashion. We formalized the notions of 1) 'discernablility' e.g., ensuring that for every 'Hamming ball', for each of its words there exists at least one spot that occurred without another word from that Hamming ball, and 2) 'recoverability' of Hamming balls. These two concepts (discernability and recoverability) jointly ensure that one can figure out which particular k-mer on a bound DNA sequence is actually bound. We ran computational simulations that indicated that most words in most Hamming balls are discernable, and that a Hamming ball is generally recoverable. This approach enables extracting any possible DNA binding site from such collections of molecules. If the collection is implemented as an array, the array can distinguish between different DNA binding sites, including similar sites.

A collection of nucleic acid molecules described herein has numerous uses. Among them is the formation of an array of oligonucleotides for studying the binding properties of a compound, e.g., a nucleic acid binding proteins. Exemplary nucleic acid binding proteins include natural and designed nucleic acid binding proteins (e.g., zinc finger proteins). Such an array of DNA oligonucleotides can be contacted by a labeled DNA binding protein; and by analyzing which oligonucleotides are bound, the sequence of the preferred binding site and the relative strengths of binding to related sites can be determined. More than one protein can be bound to such an array simultaneously. Proteins that compete or cooperate, or binding site variants of the same protein, can be bound simultaneously to analyze the binding site differences. These methods frequently use fluorescently labeled protein and fluorescent microarray scanners. Another use for these arrays is the binding of one or more proteins and the interrogation of each oligonucleotide spot with a laser for the purpose of identifying proteins using mass spectrometry. This embodiment enables identification and relative quantification of each protein bound to a given oligonucleotide, e.g., without labeling the protein.

Such a design of nucleic acid sequences is not limited to double-stranded DNA. It is also not limited to DNA microarrays, as such a set of nucleic acid sequences can also be used in solution.

In one embodiment, it is possible to use a highly parallel in vitro microarray technology for high-throughput characterization of the sequence specificities of DNA-protein interactions. We shall refer to this approach as protein binding microarray technology, or simply "PBM." PBM technology allows one to determine the binding site specificities of known, designed, or predicted transcription factors in a useful time frame, for example, in a single day. The method can include providing a purified or at least partially purified TF.

Such PBM experiments may be particularly useful when ChIP-chip experiments for particular TFs do not result in enough enrichment of bound fragments in the immunoprecipitated sample to permit identification of the DNA sites bound in vivo. The PBM data may also provide valuable data for those TFs for which it is not known under what culture conditions they are expressed or at what time points they are expressed. Moreover, there are hundreds of predicted DNA binding proteins that could be screened for sequence-specific binding using the rapid, high-throughput PBM experiments.

The advantages include the provision of numerous DNA sequence variants in a space- and cost-efficient manner. Only a minimal number of individual DNA sequences and individual DNA spots need to be synthesized. This also has implications, for example, on the required density and number of the spots on synthesized microarrays.

In another aspect, the disclosure features a collection of nucleic acid that includes all or a certain fraction (e.g., at least 70, 80, 90, 95, 98, 99% of all) intergenic sequences from a chromosome of an organism, or from a genome of an organism. Related collections can include all or a certain fraction (e.g., at least 70, 80, 90, 95, 98, 99% of all) sequence that are within a certain distance of identifiable RNA start sites, TATA boxes, Hogness boxes, Pribnow boxes, or Shine-Dalgano sequences. For example, the sequences can be between 100, 200, 500, 800, 1000, or 5000 nucleotides of such sites. The nucleic acids of the collections can be of any length, e.g., an amplifiable length, or a length ranging from 60 basepairs to 1500 basepairs or 30 by to 2400 bp, or 30 by to 200 bp. The nucleic acids can be immobilized, e.g., on one or more arrays. In some embodiments, the collection also includes nucleic acids that are intragenic, e.g., coding sequences, introns, or untranslated regulatory sequences.

In an exemplary methods, the nucleic acids of the collection are contacted to an agent, e.g., a protein, small molecule, etc., and interactions between the agent and one or more of the nucleic acids are evaluated. For example, the protein can be a transcription factor or a nucleic acid binding fragment thereof.

All references, patents, and patent applications are hereby incorporated by reference in their entireties. The following references are among those so incorporated: US 2003-0215856, US 2003-0108880, U.S. Ser. No. 60/227,900, U.S. Ser. No. 60/564,864, U.S. Ser. No. 60/587,066 (inclusive of all Appendices and Figures). and PCT/US01/26435.

DETAILED DESCRIPTION

A collection of polymers which include all or a certain percentage of all k-mers has a variety of uses. For example, the polymers can be nucleic acids or polypeptides (e.g., short peptides of length less than 50, 40, 30, 20, or 10 amino acids). The collection can be used to characterize interactions between an agent or a pool that includes multiple agents and members of the collection. The results of such characterization can indicate which k-mers interact with the agent or the pool. Although such collections of polymers have numerous applications, the following are some exemplary ones.

In one embodiment, the DNA binding specificity of a test compound, e.g., a test macromolecule such as a protein or a fragment thereof, can be characterized. For example, the DNA binding domain of a transcription factor can be contacted to members of the collection. The DNA binding domain can be labeled and the members of the collection can be disposed on an array. After contacting the domain to the array and washing the array, the array can be imaged to identify which members of the collection are bound by the domain. The method can be adapted, e.g., to identify one or more functional fragments that interact with DNA.

Results obtained with the candidate fragments can be compared to that of a larger fragment or the entire protein. Thus, information is accrued about the relative contributions of different regions of the protein to binding specificity and affinity. A similar method can be used for DNA binding domains from other types of nuclear proteins, e.g., centromeric proteins, telomeric proteins, and so forth. Protein complexes, including homo- and hetero-oligomers, can be analyzed. Likewise, RNA binding proteins or RNA binding domains thereof can be characterized using an embodiment in which the members of the collection are RNA.

The collection of polymers can be used to design a nucleic acid binding protein with a desired DNA binding specificity. A known nucleic acid binding domain or scaffold (e.g., zinc finger domains) can be randomized or specifically mutated, e.g., at DNA contacting positions. DNA contacting positions can be identified by inspection of three-dimensional structures, e.g., obtained by X-ray crystallography or NMR. These positions can be randomized, e.g., to all possible amino acids, all nineteen non-cysteine amino acids, hydrophilic amino acids, or a combination of hydrophilic and aliphatic amino acids. Mutated domains are contacted to the collection of polymers, and variants which have a desired binding specificity can be used for engineering the nucleic acid binding protein. For example, variants that interact with a site present in a target gene can be selected and used as the DNA binding domain of an artificial transcription factor that regulates that target gene. The artificial transcription factor can also include a transcriptional regulatory domain, e.g., an activation or repression domain. DNA binding domains can be constructed by linking different modules, each with a desired binding specificity, in order to produce a chimeric protein that recognizes a site. For example, one can identify or design a first polypeptide that interacts with a first k-mer and a second polypeptide that interacts with a second k-mer. Then the first and second polypeptide can linked (e.g., by a covalent or non-covalent linkage, e.g., by making a chimeric polypeptide that includes both the first and second polypeptide) to provide a protein that recognizes a site that includes the first and second k-mers. The first and second k-mers can be directly adjacent or gapped, e.g., by at least 1, 2, 3, 4, or 5 nucleotides, e.g., by one or more turns of the DNA helix.

Similar analyses can be used to characterize non-proteinaceous agents. For example, members of a chemical library or designed chemicals (e.g., polyamides and intercalators) can be evaluated, e.g., for binding specificity and affinity.

The collection of polymers can be used in implementations that do not feature an array. For example, it is possible to prepare the collection so that each polymer includes one or more invariant termini that serve as primer binding sites. The members of the collection are contained in solution, e.g., in a single container. A protein of interest can be contacted to the solution and immobilized on a solid support. After the contacting, the support can be washed to remove unbound members of the collection. The bound members can be characterized, e.g., by PCR amplification with primers that recognize the invariant termini. Amplification products can be sequenced to determine the identity of the members that bound to the protein of interest.

In addition to binding specificity, it is possible to characterize other types of interactions, e.g., enzymatic interactions. For example, a enzyme that specifically interacts with DNA can be evaluated using the collection of polymers. In one implementation, a site-specific nuclease is contacted to the collection. Members of the collection that are cleaved by the nuclease are identified. For example, if the members are present on an array and are end-labeled, the cleaved members are identified by release of the label from the respective address of the array. In other types of assays, the DNA or other nucleic acid can be modified, e.g., with a labeled molecule. Other types of enzymatic reactions that can be evaluated include methylation, acetylation (e.g., of histone bound polymers), polymerization, deamination, and so forth.

Similar applications are also available where the polymers include peptide nucleic acids (PNAs), peptides (e.g., polypeptides or short peptides), or artificial polymers (e.g., peptoids). See, e.g., Simon et al. (1992) *Proc. Natl. Acad. Sci. USA* 89:9367-71 and Horwell (1995) *Trends Biotechnol.* 13:132-4. For example, a collection of such polymers can be used to evaluate kinase specificity, e.g., by identifying which members of the collection are phosphorylated by a particular kinase. The collection can also be modified so that, rather than include all or a certain percentage of all k-mers, it includes all or a certain percentage of all k-mers with a certain property, e.g., all k-mers that include at least one serine, or all k-mers that include at least one tyrosine, or all k-mers that include at least one residue that can be phosphorylated (e.g., histidine, serine, threonine, or tyrosine). Of course, collections of polymers other than nucleic acids can also be used to evaluate binding interactions and other types interactions.

The collection of polymers can be used to identify molecules with any desired activity, e.g., a binding or other functional activity.

Polymer Arrays

A collection of polymers described herein can be immobilized on an array. An array is a substrate that includes a plurality of addresses. Each address can include a homogenous population of immobilized nucleic acids, e.g., nucleic acids of predetermined sequence. The density of addresses can be at least 10, 50, 200, 500, $10^3$, $10^4$, $10^5$, or $10^6$ addresses per $cm^2$, and/or no more than 10, 50, 100, 200, 500, $10^3$, $10^4$, $10^5$, or $10^6$ addresses/$cm^2$. Addresses in addition to addresses of the plurality can be deposited on the array. The addresses can be distributed, on the substrate in one dimension, e.g., a linear array; in two dimensions, e.g., a planar array; or in three dimensions, e.g., a three dimensional array. (e.g., layers of a gel matrix). The term "microarray" is used interchangeably with the term "array." The term "array" also refers to any coatings or surfaces on a substrate such that a molecule that is said to be "on" or physically associated with an array may be physically associated with such a coating or surface.

In one embodiment, the substrate is an insoluble or solid substrate. Potentially useful insoluble substrates include: mass spectroscopy plates (e.g., for MALDI), glass (e.g., functionalized glass, a glass slide, porous silicate glass, a single crystal silicon, quartz, UV-transparent quartz glass), plastics and polymers (e.g., polystyrene, polypropylene, polyvinylidene difluoride, poly-tetrafluoroethylene, polycarbonate, PDMS, acrylic), metal coated substrates (e.g., gold), silicon substrates, latex, membranes (e.g., nitrocellulose, nylon). The insoluble substrate can also be pliable. The substrate can be opaque, translucent, or transparent. In some embodiments, the array is merely fashioned from a multiwell plate, e.g., a 96- or 384-well microtitre plate.

A variety of methods can be used to prepare an array. In some embodiments, polymers are synthesized in situ, e.g., on the array. In other embodiments, the polymers are synthesized and then disposed on the array. The polymers are synthesized according to one of the sequence design methods described herein.

1. Light-Directed Methods

Where a single solid support is employed, the oligonucleotides can be formed using a variety of techniques known to those skilled in the art of polymer synthesis on solid supports. For example, light-directed methods are described in U.S. Pat. Nos. 5,143,854 and 5,510,270 and 5,527,681. These methods, involve activating predefined regions of a solid support and then contacting the support with a preselected monomer solution. These regions can be activated with a light source, typically shown through a mask (much in the manner of photolithography techniques used in integrated circuit fabrication). Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in PCT No. 92/10183 and U.S. Pat. No. 5,384,261. Still further techniques include bead based techniques such as those described in PCT US/93/04145 and pin based methods such as those described in U.S. Pat. No. 5,288,514.

The surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping and oxidation, the support is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced. Alternatively, an oligomer of from, for example, 4 to 30 nucleotides can be added to each of the preselected regions rather than synthesize each member one nucleotide monomer at a time.

2. Flow Channel or Spotting Methods

Additional methods applicable to array synthesis on a single support are described in U.S. Pat. No. 5,384,261. In the methods disclosed in these applications, reagents are delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

A typical "flow channel" method can generally be described as follows: Diverse polymer sequences are synthesized at selected regions of a solid support by forming flow channels on a surface of the support through which appropriate reagents flow or in which appropriate reagents are placed. For example, assume a monomer "A" is to be bound to the support in a first group of selected regions. If necessary, all or part of the surface of the support in all or a part of the selected regions is activated for binding by, for example, flowing appropriate reagents through all or some of the channels, or by washing the entire support with appropriate reagents. After placement of a channel block on the surface of the support, a reagent having the monomer A flows through or is placed in all or some of the channel(s). The channels provide fluid contact to the first selected regions, thereby binding the monomer A to the support directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the support; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the support at this stage of processing will be, for example, A, B, and AB. The process is repeated to form a vast array of sequences of desired length at known locations on the support.

After the support is activated, monomer A can be flowed through some of the channels, monomer B can be flowed through other channels, a monomer C can be flowed through still other channels, etc. In this manner, many or all of the reaction regions are reacted with a monomer before the channel block must be moved or the support must be washed and/or reactivated. By making use of many or all of the available reaction regions simultaneously, the number of washing and activation steps can be minimized. One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

The "spotting" methods of preparing compounds and arrays can be implemented in much the same manner. A first monomer, A, can be delivered to and coupled with a first group of reaction regions which have been appropriately activated. Thereafter, a second monomer, B, can be delivered to and reacted with a second group of activated reaction regions. Unlike the flow channel embodiments described above, reactants are delivered in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink-jet printer. In other embodiments, the dispenser includes a series of tubes, a manifold, an array of pipettes, or the like so that various reagents can be delivered to the reaction regions simultaneously.

3. Pin-Based Methods

Another method which is useful for the preparation of the immobilized arrays involves "pin-based synthesis." This method, which is described in detail in U.S. Pat. No. 5,288,514 utilizes a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays can often contain different reagents. Since the chemical reactions have been optimized such that each of the reactions can be performed under a relatively similar set of reaction conditions, it becomes possible to conduct multiple chemical coupling steps simultaneously. The method can use a support with a spacer, S, having active sites. In the particular case of oligonucleotides, for example, the spacer may be selected from a wide variety of molecules which can be used in organic environments associated with synthesis as well as aqueous environments associated with binding studies such as may be conducted between the nucleic acid members of the array and other molecules. These molecules include, but are not limited to, proteins (or fragments thereof), lipids, carbohydrates, proteoglycans and nucleic acid molecules. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like.

Various exemplary protecting groups are described in, for example, Atherton et al., 1989, *Solid Phase Peptide Synthesis*, IRL Press. In some embodiments, the spacer may provide for a cleavable function by way of, for example, exposure to acid or base.

b. Arrays on Multiple Supports

Yet another method which is useful for synthesis of compounds and arrays includes "bead based synthesis." A general approach for bead based synthesis is described in PCT/US93/04145 (filed Apr. 28, 1993).

c. Protein and Peptide Arrays

US 2002-0192673 describes exemplary methods for making a protein array which include protein translation. U.S. Pat. No. 5,143,854 describes methods that include synthetic amino acid coupling.

Nucleic Acid Binding Proteins

A collection of nucleic acids, as described herein, can be used to evaluate the binding properties of nucleic acid binding proteins (NABPs).

A variety of protein structures are known to bind nucleic acids with high affinity and high specificity. These structures are used in a large number of different proteins, including proteins that specifically control nucleic acid function. For reviews of structural motifs which recognize double stranded DNA, see, e.g., Pabo and Sauer (1992) *Annu. Rev. Biochem.* 61:1053-95; Patikoglou and Burley (1997) *Annu. Rev. Biophys. Biomol. Struct.* 26:289-325; Nelson (1995) *Curr Opin Genet Dev.* 5:180-9. A few non-limiting examples of nucleic acid binding domains include:

Zinc fingers. Zinc fingers are small polypeptide domains of approximately 30 amino acid residues in which there are four amino acids, either cysteine or histidine, appropriately spaced such that they can coordinate a zinc ion (For reviews, see, e.g., Klug and Rhodes, (1987) *Trends Biochem. Sci.* 12:464-469 (1987); Evans and Hollenberg, (1988) *Cell* 52:1-3; Payre and Vincent, (1988) *FEBS Lett.* 234:245-250; Miller et al., (1985) *EMBO J.* 4:1609-1614; Berg, (1988) *Proc. Natl. Acad. Sci. U.S.A.* 85:99-102; Rosenfeld and Margalit, (1993) *J. Biomol. Struct. Dyn.* 11:557-570). Hence, zinc finger domains can be categorized according to the identity of the residues that coordinate the zinc ion, e.g., as the $Cys_2$-$His_2$ class, the $Cys_2$-$Cys_2$ class, the $Cys_2$-CysHis class, and so forth. The zinc coordinating residues of $Cys_2$-$His_2$ zinc fingers have a typically spacing which is described in Wolfe et al., (1999) *Annu. Rev. Biophys. Biomol. Struct.* 3:183-212. Typically, the intervening amino acids fold to form an anti-parallel β-sheet that packs against an α-helix, although the anti-parallel β-sheets can be short, non-ideal, or non-existent. The fold positions the zinc-coordinating side chains so they are in a tetrahedral conformation appropriate for coordinating the zinc ion. The base contacting residues are at the N-terminus of the finger and in the preceding loop region. A zinc finger DNA-binding protein normally consists of a tandem array of three or more zinc finger domains.

The zinc finger domain (or "ZFD") is one of the most common eukaryotic DNA-binding motifs, found in species from yeast to higher plants and to humans. By one estimate, there are at least several thousand zinc finger domains in the human genome alone, possibly at least 4,500. Zinc finger domains can be isolated from zinc finger proteins. Non-limiting examples of zinc finger proteins include CF2-II, Kruppel, WT1, basonuclin, BCL-6/LAZ-3, erythroid Kruppel-like transcription factor, transcription factors Sp1, Sp2, Sp3, and Sp4, transcriptional repressor YY1, EGR1/Krox24, EGR2/Krox20, EGR3/Pilot, EGR4/AT133, Evi-1, GLI1, GLI2, GLI3, HIV-EP1/ZNF40, HIV-EP2, KR1, ZfX, ZfY, and ZNF7.

Computational methods described below can be used to identify all zinc finger domains encoded in a sequenced genome or in a nucleic acid database. Any such zinc finger domain can be utilized. In addition, artificial zinc finger domains have been designed, e.g., using computational methods (e.g., Dahiyat and Mayo, (1997) *Science* 278:82-7).

Homeodomains. Homeodomains are simple eukaryotic domains that consist of a N-terminal arm that contacts the DNA minor groove, followed by three α-helices that contact the major groove (for a review, see, e.g., Laughon, (1991) *Biochemistry* 30:11357-67). The third α-helix is positioned in the major groove and contains critical DNA-contacting side chains. Homeodomains have a characteristic highly-conserved motif present at the turn leading into the third α-helix. The motif includes an invariant tryptophan that packs into the hydrophobic core of the domain. Homeodomains are commonly found in transcription factors that determine cell identity and provide positional information during organismal development. Such classical homeodomains can be found in the genome in clusters such that the order of the homeodomains in the cluster approximately corresponds to their expression pattern along a body axis. Homeodomains can be identified by alignment with a homeodomain, e.g., Hox-1, or by alignment with a homeodomain profile or a homeodomain hidden Markov Model (HMM; see below), e.g., PF00046 of the Pfam database or "HOX" of the SMART database (see online resources referenced in Letunic et al. (2004) Nucleic Acids Res. 2004 Jan. 1; 32 Database issue:D142-4), or by the Prosite motif PDOC00027 as mentioned above.

Helix-turn-helix proteins. This DNA binding motif is common among many prokaryotic transcription factors. There are many subfamilies, e.g., the Lad family, the AraC family, to name but a few. The two helices in the name refer to a first α-helix that packs against and positions a second α-helix in the major groove of DNA. These domains can be identified by alignment with a HMM, e.g., HTH_ARAC, HTH_ARSR, HTH_ASNC, HTH_CRP, HTH_DEOR, HTH_DTXR, HTH_GNTR, HTH_ICLR, HTH_LACI, HTH_LUXR, HTH_MARR, HTH_MERR, and HTH_XRE profiles available in the SMART database.

Helix-loop-helix proteins. This DNA binding domain is commonly found among homo- and hetero-dimeric transcription factors, e.g., MyoD, fos, jun, E11, and myogenin. The domain consists of a dimer, each monomer contributing two α-helices and intervening loop. The domain can be identified by alignment with a HMM, e.g., the "HLH" profile available in the SMART database. Although helix-loop-helix proteins are typically dimeric, monomeric versions can be constructed by engineering a polypeptide linker between the two subunits such that a single open reading frame encodes both the two subunits and the linker.

Some nucleic acid binding domains can bind to both DNA and RNA. For example, certain zinc finger domains and homeodomains can interact with RNA as well as DNA. In addition, a number of RNA binding domains, both natural and artificial, are known. For example, the HIV tat protein includes an RNA binding domain that is arginine rich. See generally, Tian et al. (2003) Prog Nucleic Acid Res Mol Biol. 74:123-58; Das et al. (2003) Biopolymers. 70(1):80-5; and Doyle et al. (2002) J Struct Biol. 140(1-3):147-53.

Identification of Protein Domains

A variety of methods can be used to identify structural domains, e.g., nucleic acid binding domains.

Computational Methods. The amino acid sequence of a DNA binding domain isolated by a method described herein can be compared to a database of known sequences, e.g., an annotated database of protein sequences or an annotated database which includes entries for nucleic acid binding domains. In another implementation, databases of uncharacterized sequences, e.g., unannotated genomic, EST or full-length cDNA sequence; of characterized sequences, e.g., SwissProt or PDB; and of domains, e.g., Pfam, ProDom (Servant et al (2002) Brief Bioinform. 2002 Sep.; 3(3):246-51 and SMART (Simple Modular Architecture Research Tool, see above) can provide a source of nucleic acid binding domain sequences. Nucleic acid sequence databases can be translated in all six reading frames for the purpose of comparison to a query amino acid sequence. Nucleic acid sequences that are flagged as encoding candidate nucleic acid binding domains can be amplified from an appropriate nucleic acid source, e.g., genomic DNA or cellular RNA. Such nucleic acid sequences can be cloned into an expression vector. The procedures for computer-based domain identification can be interfaced with an oligonucleotide synthesizer and robotic systems to produce nucleic acids encoding the domains in a high-throughput platform. Cloned nucleic acids encoding the candidate domains can also be stored in a host expression vector and shuttled easily into an expression vector, e.g., into a translational fusion vector with Zif268 fingers 1 and 2, either by restriction enzyme mediated subcloning or by site-specific, recombinase mediated subcloning (see U.S. Pat. No. 5,888,732). The high-throughput platform can be used to generate multiple microtitre plates containing nucleic acids encoding different candidate nucleic acid binding domains.

Detailed methods for the identification of domains from a starting sequence or a profile are well known. See, for example, Prosite (Hofmann et al., (1999) *Nucleic Acids Res.* 27:215-219), FASTA, BLAST (Altschul et al., (1990) *J. Mol. Biol.* 215:403-10.), etc. A simple string search can be done to find amino acid sequences with identity to a query sequence or a query profile, e.g., using Perl to scan text files. Sequences so identified can be about 30%, 40%, 50%, 60%, 70%, 80%, 90%, or greater identical to an initial input sequence.

Domains similar to a query domain can be identified from a public database, e.g., using the XBLAST programs (version 2.0) of Altschul et al., (1990) *J. Mol. Biol.* 215:403-10. For example, BLAST protein searches can be performed with the XBLAST parameters as follows: score=50, wordlength=3. Gaps can be introduced into the query or searched sequence as described in Altschul et al., (1997) *Nucleic Acids Res.* 25(17):3389-3402. Default parameters for XBLAST and Gapped BLAST programs are available from on-line resources of the National Center of Biotechnology Information, National Institutes of Health, Bethesda Md.

The Prosite profiles PS00028 and PS50157 can be used to identify zinc finger domains. In a SWISSPROT release of 80,000 protein sequences, these profiles detected 3189 and 2316 zinc finger domains, respectively. Profiles can be constructed from a multiple sequence alignment of related proteins by a variety of different techniques. Gribskov and coworkers (Gribskov et al., (1990) *Meth. Enzymol.* 183:146-159) utilized a symbol comparison table to convert a multiple sequence alignment supplied with residue frequency distributions into weights for each position. See, for example, the PROSITE database and the work of Luethy et al., (1994) *Protein Sci.* 3:139-1465.

Hidden Markov Models (HMM's) representing a DNA binding domain of interest can be generated or obtained from a database of such models, e.g., the Pfam database, release 2.1. A database can be searched, e.g., using the default parameters, with the HMM in order to find additional domains (see, e.g., the Sanger Center, Cambridge UK for default parameters). Alternatively, the user can optimize the parameters. A threshold score can be selected to filter the database of sequences such that sequences that score above the threshold are displayed as candidate domains. A description of the Pfam database can be found in Sonhammer et al., (1997) *Proteins* 28(3):405-420, and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235: 1501-1531; and Stultz et al., (1993) *Protein Sci.* 2:305-314.

The SMART database of HMM's (Simple Modular Architecture Research Tool, available from online resources of EMBL, Heidelberg, Germany; Schultz et al., (1998) *Proc. Natl. Acad. Sci. USA* 95:5857 and Schultz et al., (2000) *Nucl. Acids Res* 28:231) provides a catalog of zinc finger domains (ZnF_C2H2; ZnF_C2C2; ZnF_C2HC; ZnF_C3H1; ZnF_C4; ZnF_CHCC; ZnF_GATA; and ZnF_NFX) identified by profiling with the hidden Markov models of the HMMer2 search program (Durbin et al., (1998) *Biological sequence analysis: probabilistic models of proteins and nucleic acids*. Cambridge University Press).

Hybridization-based Methods. A collection of nucleic acids encoding various forms of a DNA binding domain can be analyzed to profile sequences encoding conserved amino- and carboxy-terminal boundary sequences. Degenerate oligonucleotides can be designed to hybridize to sequences encoding such conserved boundary sequences. Moreover, the efficacy of such degenerate oligonucleotides can be estimated by comparing their composition to the frequency of possible annealing sites in known genomic sequences. Multiple rounds of design can be used to optimize the degenerate oligonucleotides.

A library of nucleic acid domains can be constructed by isolation of nucleic acid sequences encoding domains from genomic DNA or cDNA of eukaryotic organisms such as humans. Multiple methods are available for doing this. For example, a computer search of available amino acid sequences can be used to identify the domains, as described above. A nucleic acid encoding each domain can be isolated and inserted into a vector appropriate for the expression in cells, e.g., a vector containing a promoter, an activation domain, and a selectable marker. In another example, degenerate oligonucleotides that hybridize to a conserved motif are used to amplify, e.g., by PCR, a large number of related domains containing the motif. Moreover, screening a collection limited to domains of interest, unlike screening a library of unselected genomic or cDNA sequences, significantly decreases library complexity and reduces the likelihood of missing a desirable sequence due to the inherent difficulty of completely screening large libraries. Domains in such libraries can be characterized, e.g., using the methods described herein.

Engineering Nucleic Acid Binding Specificity

It is possible to use the collection of polymers described herein to characterize, screen and select modified proteins. For example, known nucleic acid binding proteins can be mutated, e.g., by randomizing one or more positions or by making site specific mutations (e.g., a substitution, insertion, and/or deletion). Such modified proteins can then be contacted to a collection of polymers, either individually or in groups.

Any suitable method known in the art can be used to modify, design and construct nucleic acids encoding NABPs, e.g., phage display, random mutagenesis, combinatorial libraries, computer/rational design, affinity selection, PCR, cloning from cDNA or genomic libraries, synthetic construction and the like. Examples of site specific mutations include modifying a DNA contacting residue, e.g., to alanine, or to a different hydrophilic amino acids. For example, some modifications change the size of the side chain. Examples of randomizations include completely random representation of amino acids (e.g., all amino acids of a set can occur with equal probability, or a probability that is a function of their codon usage and the set of allowed codons), or partially random, e.g., by biasing nucleotides or codons, e.g., to favor certain amino acids (e.g., wildtype amino acids) relative to others. Randomization can occur at one or more positions. For example, at least 25, 50, or 75% of the DNA contacting positions can be randomized, or all such positions can be randomized.

Randomization can be used to produce a library, e.g., a phage display library, from which useful variants can be identified. The library can be screened, e.g., using a desired target that is immobilized. The library as a whole or a subset of the library can be contacted to the collection of polymers, e.g., to provide information about the library's collective ability to interact with different k-mers.

One example of a nucleic acid binding protein that can be altered to produce an artificial transcription factor is a protein that includes one or more zinc finger domains. Such domains are typically arranged as an array of at least three fingers. Nucleic acid binding region of such proteins can be prepared by selection in vitro (e.g., using phage display) or in vivo, or by design based on a recognition code (see, e.g., WO 00/42219 and U.S. Pat. No. 6,511,808). See, e.g., Rebar et al. (1996) Methods Enzymol 267:129; Greisman and Pabo (1997) Science 275:657; Isalan et al. (2001) Nat. Biotechnol 19:656; and Wu et al. (1995) Proc. Nat. Acad. Sci. USA 92:344 for, among other things, methods for creating libraries of varied zinc finger domains. See also, e.g., U.S. Pat. No. 5,789,538; U.S. Pat. No. 6,453,242; U.S. 2003-0165997; Wu et al., PNAS 92:344-348 (1995); Jamieson et al., Biochemistry 33:5689-5695 (1994); Rebar & Pabo, Science 263:671-673 (1994); Choo and Klug, PNAS 91:11163-11167 (1994); Choo and Klug, PNAS 91:11168-11172 (1994); Desjarlais & Berg, PNAS 90:2256-2260 (1993); Desjarlais and Berg, PNAS 89:7345-7349 (1992); Pomerantz et al., Science 267: 93-96 (1995); Pomerantz et al., PNAS 92:9752-9756 (1995); and Liu et al., PNAS 94:5525-5530 (1997); Griesman and Pabo, Science 275:657-661 (1997); Desjarlais and Berg, PNAS 91:11-99-11103 (1994).

Non-Proteinaceous Nucleic Acid Binding Compounds

A collection of polymers described herein can also be used to evaluate, design, and test non-proteinaceous nucleic acid binding compounds and other agents which interact with nucleic acids. The polymers can be used, e.g., to evaluate the degree of specificity of an agent for particular sequences. Specificity may vary across a continuum from completely non-specific to broad to highly sequence specific. Again, interactions other than binding interactions can also be evaluated.

One class of compounds which can specifically interact with nucleic acid is the class of polyamides, which includes pyrrole-imidazole polyamides. See, e.g., generally, Dervan et al. (2003) "Recognition of the DNA minor groove by pyrrole-imidazole polyamides." Curr Opin Struct Biol. 13(3):284-99. See also, e.g., U.S. Ser. No. 08/607,078, PCT/US97/03332, U.S. Ser. Nos. 08/837,524, 08/853,525, PCT/US97/12733, U.S. Ser. No. 08/853,522, PCT/US97/12722, PCT/US98/06997, PCT/US98/02444, PCT/US98/02684, PCT/US98/01006, PCT/US98/03829, and PCT/US98/0714. As described in the foregoing references, polyamides comprise polymers of amino acids covalently linked by amide bonds. Preferably, the amino acids used to form these polymers include N-methylpyrrole (Py) and N-methylimidazole (Im). Polyamides containing pyrrole (Py), and imidazole (Im) amino acids are synthetic ligands that have an affinity and specificity for DNA comparable to naturally occurring DNA binding proteins Trauger, J. W., Baird, E. E. & Dervan, P. B. (1996), Nature 382, 559-561; Swalley, S. E., Baird, E. E. & Dervan, P. B. (1997), J. Am. Chem. Soc. 119, 6953-6961; Turner, J. M., Baird, E. E. & Dervan, P. B. (1997), J. Am. Chem. Soc. 119, 7636-7644; Trauger, J. W., Baird, E. E. & Dervan, P. B. (1998), Angewandte Chemie-International Edition 37, 1421-1423; and Dervan and Burli (1999), Current Opinion in Chemical Biology 3, 688-693. See, e.g., U.S. Pat. No. 6,559,125. Polyamines can be conformationally constrained and also derivatized, e.g., to enable conjugation to another moiety, e.g., a protein.

Other types of non-proteinaceous agents include other nucleic acids, e.g., nucleic acids that can form a triple helix that interacts with a duplex. For example, U.S. Pat. No. 6,432,638 discloses homopyrimidinepolydeoxyribonucleotide probes with at least one detectable marker, chemotherapeutic agent or a DNA-cleaving moiety attached to at least one predetermined position. See also U.S. Pat. No. 6,403,302 to Dervan et al. The probes are said to be capable of binding the corresponding homopyrimidine-homopurine tracts within large double-stranded nucleic acids by triple-helix formation at a predetermined site, and can be used for gene therapy.

Characterizing Nucleic Acid Binding

After evaluating interaction of an agent to a collection of nucleic acids (e.g., DNAs or RNAs), one can further characterize interaction of the agent to one or more particular members, e.g., individually, or a particular k-mer. For example, further characterization can be used to determine qualitative or quantitative parameters that describe in the interaction between the agent and a member of the collection, e.g., binding parameters, such as binding kinetics and dissociation constants. Further characterization can also provide more sequence information, e.g., by determining the degree of specificity of the agent for a particular identified k-mer or other sequence. Examples of such methods include: Electrophoretic Mobility Shift Assay (EMSA), footprinting, surface plasmon resonance, and methylation interference.

Electrophoretic Mobility Shift Assay (EMSA). Electrophoretic mobility shift assays can be used to characterize interactions between proteins and nucleic acids. For example, electrophoretic mobility shift assay (EMSA) can be performed as described previously (see, e.g., Durand et al., Mol. Cell. Biol. 8:1715-1724, and Jones et al., Cell 42:5593 (1985). In one implementation, binding reactions (15 µl final volume) contain 10 mM Tris-HCl (pH 7.5), 80 mM sodium chloride, 1 mM dithiothreitol, 1 mM EDTA, 5% glycerol, 1.5-2 µg of poly(dI•dC), 5 to 10 µg of the protein agent, and 20,000 cpm (0.1 to 0.5 ng) of $^{32}$P-end-labeled probe (e.g., a double-stranded oligonucleotide probe). After incubation for 45-60 min on ice, the protein-probe complexes were resolved on nondenaturing 5% polyacrylamide gels run in 1× Tris-borate-EDTA (TBE) buffer (Ausubel et al., Green Publishing Associates and Wiley-Interscience, New York (1987)). Oligonucleotide probes can be labeled using the Kienow fragment. For cold oligonucleotide competition assays, a 1,000-fold molar excess of unlabeled probe (identical to, related to, or unrelated to the probe) can be added to the binding reaction mixture 15 min into the incubation, and the mixture can be further incubated for 30 min at 4° C. prior to gel loading.

DNAse I Footprinting Assay. DNase I footprinting can be used to assay for DNA sequences which could be protected from DNase I digestion by an agent. Related methods are available for analyzing RNA. See, e.g., Siegel (1988) Proc Natl Acad Sci U S A. 85(6):1801-5. A negative and positive control can be run on either side of the agent of interest to produce adequate points of reference.

In one implementation, DNAse I footprinting is performed using a derivation of the procedures described by Durand et al., Mol. Cell. Biol. 8:1715 (1988) and Jones et al., Cell 42:5593 (1985). Binding reactions are carried out under the conditions described above for EMSA but scaled up to 50 µl. After binding, using 50 µg nuclear extracts, 50 µl of a 10 mM MgCl$_2$/5 mM CaCl$_2$ solution is added and 2 µl of an appropriate DNAse I (Worthington, Freehold, N.J.) dilution is added and incubated for 1 minute on ice. DNase I digestion is stopped by adding 90 µl of stop buffer (20 mM EDTA, 1% SDS, 0.2 M NaCl). After addition of 20 µg yeast tRNA as carrier, the samples are extracted two times with an equal volume of phenol/chloroform (1:1) and precipitated after adjusting the solution to 0.3 M sodium acetate and 70% ethanol. DNA samples are then resuspended in 4 µl of an 80% formamide loading dye containing 1×TBE, bromophenol blue and xylene cyanol, heated to 90° C. for 2 minutes, and loaded on 6% polyacrylamide-urea sequencing gels.

Methylation interference can be assayed according to the protocol of Baldwin (Ausubel, F. M., et al., Green Publishing Associates and Wiley-Interscience, New York (1987)). First, a preparative EMSA (10-fold scale up of reaction described above) is performed. Then, the nucleic acid probe (typically DNA) is eluted from the excised bands representing EMSA complexes by electroelution in a Bio-Rad apparatus. Following piperidine cleavage, the DNA ladders were analyzed on standard 10% polyacrylamide-urea sequencing gels (Ausubel, F. M., et al, Green Publishing Associates and Wiley-Interscience, New York (1987)).

UV Crosslinking Analysis. Preparative EMSA can be performed as described for methylation interference. Before autoradiography, the gel is exposed to UV light in a STRATALINKER™ (Stratagene, La Jolla, Calif.), e.g., as described previously (Kelsumi et al., Mol. Cell. Biol. 13:6690-6701 (1993)). Bands are excised and heated to 70° C. in Laemmli sample buffer. Gel slices are loaded into the walls of a sodium dodecyl sulfate 10% polyacrylamide electrophoresis (SDS-10% PAGE) gel run in glycine-SDS buffer (Ausubel, F. M., et al, Green Publishing Associates and Wiley-Interscience, New York (1987)).

Interaction Profiling

In one aspect, the disclosure features a method of providing an interaction site profile. The method includes providing an array of polymers, e.g., using a collection of polymers described herein, contacting the compound with the array, and identifying polymers to which the compound interacts, thus providing a "raw" interaction site profile. The array includes a plurality of polymers, wherein the plurality includes all or a certain percentage of all k-mers. Typically, each polymer is positionally distinguishable from the other probes.

The term "raw" interaction site profile refers to the profile which indicates interaction between the compound and each polymer of the plurality. In one embodiment, the interaction of the compound with the probe results in a covalent modification of the probe, e.g., a covalent bond of the probe can be broken or formed. In a preferred embodiment, the interaction of the compound with the capture probe is a binding interaction wherein neither the compound nor the probe has a covalent bond broken or formed.

In one embodiment, the raw interaction site profile is a list of objects, each object representing one of the polymers of the array, and having an associated value, preferably a numerical value. The list can contain two, three, four, five, six, seven, eight, nine, ten, 15, 20, 50, 100, 1000 or more objects. In a preferred embodiment, each polymer on the array is represented by an object. In this embodiment, the list includes as many objects as there are polymers, e.g., addresses on the array. In another embodiment, the list includes the polymers which interact with the compound. Thus, the list can contain only those polymers for which an interaction was detected, or only those polymers for which an interaction met a predetermined condition. Such a list has fewer objects as members than the number of unique polymers.

The raw profile can be processed, e.g., to determine which k-mer or k-mers the compound interacts with. The results of the processing can be provided in the form of a processed profile.

The results of the processing can be in the form of a processed profile which represents k-mers with which the compound interacts. In one embodiment, the processed profile is a list of objects, each object representing one of the k-mers in the collection on the array, and having an associated value, preferably a numerical value. The list can contain two, three, four, five, six, seven, eight, nine, ten, 15, 20, 50, 100, 1000 or more objects. In a preferred embodiment, each k-mer in the collection is represented by an object. In this embodiment, the list includes as many objects as there are k-mers, e.g., as represented on the array. In another embodiment, the list includes the k-mers which interact with the compound. Thus, the list can contain only those k-mers for which an interaction was detected, or only those k-mers for which an interaction met a predetermined condition.

In a preferred embodiment, the raw profile and/or the processed profile is stored in computer memory, such as random access memory or flash memory, or on computer readable media, such as magnetic (e.g., a diskette, removable hard drive, or internal hard drive) or optical media (e.g., a compact disk (CD), DVD, or holographic media). A profile stored in this manner can be on a personal computer, server, e.g., a network server, or mainframe, and can be accessed from another device across a network, e.g., an intranet or internet. In another embodiment, the raw or processed profile is printed on to a media such as a plastic, a paper or a label, e.g., as a bar code or variation thereof.

The value associated with each object of an interaction site profile can be obtained from a quantitative observation, or a qualitative observation, preferably a quantitative observation. In one embodiment, the associated value is a function of the amount of interaction between the compound and a polymer. For example, the amount of interaction can be the amount of binding, the amount of polymer modification, or affinity. In a preferred embodiment, the associated value is a function of the amount of binding between the compound and the polymer. The value can be a function of the amount of a quantitative observation such as a fluorescent signal, a radioactive signal, or a phosphorescent signal of a contacted polymer. The value can be provided by an instrument, e.g., a CCD camera. In one embodiment, the value is a function of the surface plasmon resonance at the site of a contacted polymer. In a preferred embodiment, the associated values are adjusted for a background signal. In another embodiment, the associated value is a function of moles of bound compound. In yet another embodiment, the associated value is an affinity, relative affinity, apparent affinity, association constant, dissociation constant, logarithm of an affinity, or free energy for binding, of the compound for the particular polymer. In a preferred embodiment, the associated values in the list are differ. In other words, the list contains more than one object, and e.g., the associated values of the objects in the list are not all the same. The values provide a range. The values can be distributed in the range. In some embodiments, the values can approximate a Poisson distribution. The list can contain objects whose associated values are zero, or null. The list can contain objects whose associated values are positive or negative. In one embodiment, the list does not contain any objects whose associated values are zero or null.

In a preferred embodiment, interaction site profiles are provided for a compound at varying concentrations of the compound, e.g. an interaction site profile is provided for a compound at a first concentration, at a second concentration, etc. In another preferred embodiment, interaction site profiles are provided for a compound for interaction with varying concentration of polymers. For example, an array can have more than one unit, the compositions of the units being identical, but the first unit having the polymers at a first concentration, and the second unit having the polymers at a second concentration, etc. In yet another preferred embodiment, interaction site profiles are provide for a compound for various intervals after contacting the compound to the array. For example, a first profile can be provided after a first interval of time has elapsed after contacting, and a second profile can be provided after a second interval, etc.

An interaction site profile (e.g., a raw and/or processed profile) can be generated for any compound, e.g., a protein, a peptoid, a PNA, or a chemically modified protein. In a much preferred embodiment the compound is a protein. The polypeptide can be a nucleic acid binding protein. In one embodiment, the protein is an RNA contacting protein such as a splicing factor, a ribosomal protein, a viral protein, an RNA modification enzyme, a translation factor, and the like. In a preferred embodiment, the protein is a DNA contacting protein such as a transcription factor, a replication factor, a telomere binding protein, a centromere binding protein, a restriction modification enzyme, a DNA methylase, DNA repair protein, a single-stranded DNA binding protein, a recombination protein and the like. In one embodiment, the protein is a transcription factor. The transcription factor can bind a double stranded DNA sequence with an affinity of 10 mM, 1 mM, 100 nM or less, preferably 10 nM or less, 1 nM or less, and even more preferably 100 pM or less. The transcription factor can be selected from the group consisting of homeodomains, helix-turn-helix motif proteins, beta-sheets, leucine zippers, steroid receptors, and zinc finger proteins. In one embodiment, the protein is modified or combined with natural and exotic chemical ligands. In yet another embodiment, the compound for which the interaction site profile is generated includes more than one protein, e.g., a complex of proteins.

In a preferred embodiment, the protein is covalently attached to bacteriophage, e.g., a T7 phage, a lambdoid phage, or a filamentous phage. Preferably, the protein is covalent attached to a filamentous phage such as fd or M13. The protein can be covalently fused to a coat protein by constructing a fusion gene with the gene encoding the polypeptide an the viral coat protein gene, e.g., filamentous phage gene VIII or gene III. In another preferred embodiment, the polypeptide is covalently attached to green fluorescent protein (GFP), or a variant thereof (such as enhanced GFP, CFP, BFP, and the like). The protein can be covalently attached by constructing a fusion gene. In yet another embodiment, the protein is linked with an unrelated sequence, e.g., a fusion protein, purification handle, or epitope tag. Useful examples of such unrelated sequences include maltose binding protein, glutathione-S-transferase, chitin binding protein, thioredoxin, hexa-histidine (or 6-His), the "FLAG tag," the myc epitope, and the hemagglutinin epitope.

In one embodiment, the protein contains a detectable label. The detectable label can be a radiolabel. Preferably, the detectable label is a fluorescent label, e.g., malachite green, Oregon green, Texas Red, Congo Red, Cy3, SYBRGREEN™ I, or R-phycoerythrin. In another embodiment, the protein is contacted with an antibody. The antibody can contact the protein directly or can contact a covalently attached tag, e.g., a moiety mentioned above.

In a preferred embodiment, the protein is a variant of a natural counterpart. The variant can have at least one amino acid difference from the natural counterpart. Preferably the differing amino acid is located within 50 Ångstroms, 20 Ångstroms, or 10 Ångstroms or less of the bound nucleic acid in a structural model, e.g., a model built from X-ray diffraction data, NMR restraint data, or another homology model.

Quality Control of Protein Production

A collection of polymers described herein can be used to evaluate protein production. For example, the interactions of a purified protein or partially purified protein and molecules of the collection can be evaluated and compared to a reference, e.g., a previous production run or previous sample of the protein. For example, when producing a pharmaceutical compound, e.g., a protein therapeutic, the compound is typically purified from cruder mixture, e.g., a cell lysate or media that contains a cell secretion. Without needing to know the contents of any particular sample, the interactions between a sample and the molecules of the collection can provide information about its contents and the degree of purity of the desired product, e.g., the protein therapeutic. Impurities may interact with different molecule in the collection than the desired product and will be detected. Accordingly, when doing numerous production runs to produce a desired product, a sample of the final product or samples from earlier purification steps can be evaluated by contacting to molecules in the collection.

Receptor Ligands

A collection of peptides that includes all or a certain percentage of all possible k-mers can be used to identify a ligand for receptor. In one exemplary implementation, the peptides in the collection are located on different addresses of an array. A soluble form of the receptor is produced, e.g., by expressing the extracellular domain, a fragment thereof or a version of the protein lacking the transmembrane domain. The soluble receptor (e.g., labeled receptor) is contacted to the array and locations where the receptor interacts with a peptide are detected. A peptide that includes only the relevant k-mer can be synthesized and further characterized, e.g., by contacting the peptide to a cell that expresses the receptor and evaluating a biological function of the cell.

Delivering Nucleic Acid Binding Proteins

As described herein, a collection of polymers that includes all or a certain percentage of all k-mers can be used to design, select or identify a nucleic acid binding protein, e.g., an engineered nucleic acid binding protein. The protein may have therapeutic or diagnostic uses, e.g., for detecting, preventing, or ameliorating diseases or disorders in a subject or in cells of a subject.

Conventional viral and non-viral based gene transfer methods can be used to introduce nucleic acids encoding engineered NABP in mammalian cells or target tissues.

Such methods can be used to administer nucleic acids encoding NABPs to cells in vitro. Preferably, the nucleic acids encoding NABPs are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808-813 (1992); Nabel and Feigner, TIBTECH 11:211-217 (1993); Mitani and Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer and Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids encoding engineered NABPs include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787, and 4,897,355) and lipofection reagents are sold commercially (e.g., TRANSFECTAM™ and LIPOFECTIN™. Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered NABP can exploit the highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of NABPs could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J Virol. 66:1635-1640 (1992); Sommerfelt et al, Virol. 176:58-59 (1990); Wilson et al., J. Virol. 63:2374-2378 (1989); Miller et al., J. Virol. 65:2220-2224 (1991); PCT/US94/05700).

In applications where transient expression of the NABP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin et al., Mol Cell. Biol. 4:2072-2081 (1984); Hermonat and Muzyczka, PNAS 81:6466-6470 (1984); and Samulski et al., J. Virol. 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial (Blaese et al., Science 270:475480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., Lancet 351(9117) 1702-3 (1998), Kearns et al., Gene Ther. 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al, Infection 24(1) 5-10 (1996); Sterman et al., Hum. Gene Ther. 9(7) 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus, expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a NABP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ, and TNF-α are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and Iad (differentiated antigen presenting cells) (see Inaba et al., J. Exp. Med. 176:1693-1702 (1992)).

Vectors (e.g., retroviruses, adenoviruses, liposomes, etc.) containing therapeutic NABP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. There is a wide variety of suitable formulations for pharmaceutical compositions, as described herein and, e.g., in Remington's Pharmaceutical Sciences, 17th ed., 1989).

Delivery Vehicles for NABPs

An important factor in the administration of polypeptide compounds, such as the NABPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as NABPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270:14255-14258 (1995)).

Examples of peptide sequences which can be linked to a NABP, for facilitating uptake of NABP into cells, include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot and O'Hare, Cell 88:223-233 (1997)). Other suitable chemical moieties that provide enhanced cellular uptake may also be chemically linked to NABPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas exotoxin* A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., J. Biol. Chem., 268:3334-3341 (1993); Perelle et al., Infect. Immun., 61:5147-5156 (1993); Stenmark et al., J. Cell Biol. 113:1025-1032 (1991); Donnelly et al., PNAS 90:3530-3534 (1993); Carbonetti et al., Abstr. Annu. Meet. Am. Soc. Microbiol. 95:295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Such subsequences can be used to translocate NABPs across a cell membrane. NABPs can be conveniently fused to or derivatized with such sequences. Typically, the translocation sequence is provided as part of a fusion protein. Optionally, a linker can be used to link the NABP and the translocation sequence. Any suitable linker can be used, e.g., a peptide linker.

The NABP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, e.g., a NABP.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a NABP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g. PNAS 84:7851 (1987); Biochemistry 28:908 (1989)). When liposomes are endocytosed by a target cell, for example, they become destabilized and release their contents. This destabilization is termed filsogenesis. Dioleoylphosphatidylethanolamine (DOPE) is the basis of many "fusogenic" systems.

Such liposomes typically comprise a NABP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer and Bangham, Biochim. Biophys. Acta 443:629-634 (1976); Fraley et al., PNAS 76:3348-3352 (1979); Hope et al, Biochim. Biophys. Acta 812:55-65 (1985); Mayer et al., Biochim. Biophys. Acta 858: 161-168 (1986); Williams et al, PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target the liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

EXAMPLES

Example 1

General Discussion of One Implementation

We have developed a new, highly parallel in vitro microarray technology for high-throughput characterization of the sequence specificities of DNA-protein interactions. We shall refer to this approach as protein binding microarray (PBM) technology. PBM technology allows evaluating interactions between agents and nucleic acids, for example, the measurement of direct or indirect binding of agents, such as epitope-tagged transcription factors to nucleic acids on DNA microarrays spotted with double-stranded DNAs containing potential DNA binding sites. For instance, a DNA binding protein of interest is expressed with an epitope tag. The tag facilitates protein purification and detection. The epitope-tagged DNA binding protein (usually at least partially purified) is applied to a double-stranded DNA microarray. The microarray is then washed gently to remove any nonspecifically bound protein. The protein-bound microarray is then labeled with a primary antibody specific for the epitope tag expressed as a fusion with the DNA binding protein.

PBM technology enables evaluating the binding site specificities of a nucleic acid binding protein in a single day, starting from the purified protein. Using compact microarrays, we can determine the relative binding affinities for all possible 9-mers using a single nucleic acid array. PBM technology is highly scalable, as many assays may be performed in a single day. Moreover, it is a universal system, since the same nucleic acid array can be used to evaluate proteins from any species for binding to sites in any genome. One person could, for instances, perform triplicate PBM assays with multiple proteins in one day. DNA arrays can be printed, e.g., in production quantities. Identical arrays can be used for triplicate array experiments for each protein of interest.

We have successfully purified FLAG-tagged Rpn4 fusion protein from *E. coli* using anti-FLAG M2 affinity gel (Sigma). We used this purified Rpn4 fusion protein in EMSAs successfully, indicating that the dual-tagged Rpn4 fusion protein binds DNA sequence-specifically. We have also used this FLAG-tagged RPN4 in PBM experiments to evaluate strategies such as crosslinking the protein-bound microarrays before labeling with a fluorophore conjugate. For labeling protein-bound PBMs, we evaluated a number of strategies, including: (1) labeling with the M2 anti-FLAG primary antibody (Sigma), followed by R-phycoerythrin-conjugated secondary antibody (Sigma); (2) labeling the protein-bound PBMs with FITC- or Cy3-conjugated anti-FLAG antibody (Sigma); (3) Alexa488-conjugated M2 anti-FLAG primary antibody (Sigma). Detection can employ a standard microarray scanners (GSI Lumonics SCANARRAY™) equipped with the appropriate lasers and filter sets. We have seen that higher signal intensity is indicative of higher DNA-protein binding affinity. Thus, PBM technology is successful in identifying sequence-specific TF binding. We also found that labeling with a fluorophore-conjugated primary antibody results in high quality data with a broad dynamic range of signal intensities.

We have used GST-tagged yeast TFs in PBM experiments using these microarrays. The washed, protein-bound microarrays are labeled with a primary anti-GST antibody conjugated with the fluorophore Alexa488. The washed arrays are then scanned using a GSI Lumonics SCANARRAY™ microarray scanner. The microarray images are quantified using GENEPIX™ microarray image quantitation software (Axon Instruments, Inc.). The sequences corresponding to the spots with a Bonferroni-corrected p-value<=0.001 are run through a motif finding program to identify the TF's binding site motif We use an integrated motif finder that combines results from MEME™, MDSCAN™, BIOPROSPECTOR™, and ALIGNACE™. We identified both ungapped (e.g., Rap1 and Mig1) and gapped (e.g., Abf1) DNA binding site motifs. Experimental negative controls, using either GST alone or a GST-fusion to a protein that is not DNA binding, do not result in 'bound' spots on the microarray. Computational negative controls, in which randomly selected yeast intergenic regions are searched with motif finding programs, do not result in motifs with significant group specific scores, meaning that any low scoring motifs that do arise from these random sets are not specific to the input set of motifs (the motifs arising from the spots 'bound' in our PBMs are highly specific to the set of 'bound' spots).

Survey of TF DNA Binding Domain Types:

The table below exemplifies some of the major classes of eukaryotic DNA binding proteins, with the approximate number of proteins as well as the number of domains of each type in the human, fly, and yeast genomes.

| Domain type | Human | Fly | Yeast |
| --- | --- | --- | --- |
| C2H2 zinc finger | 564 (4500) | 234 (771) | 34 (56) |
| Homeobox domain | 160 (178) | 100 (103) | 6 |
| Helix-loop-helix DNA binding domain | 60 (61) | 44 | 4 |
| Basic leucine zipper (bZIP) | ~55 a | 27 b | ~20 d |
| Nuclear hormone receptor | 47 | 17 | 0 |
| Fork head domain | 35 (36) | 20 (21) | 4 |
| Myb-like DNA-binding domain | 32 (43) | 18 (24) | 15 (20) |
| Ets family | ~22 e | ~8 c | ~0 d |
| C2CH zinc finger | 17 (22) | 6 (8) | 3 (5) |
| Paired domain | ~9 e | ~17 c | ~0 d |
| GATA zinc finger | 11 (17) | 5 (6) | 9 |
| Zn(2)-Cys(6) binuclear cluster (fungal) | | 0 e | 0 c ~11 d |
| MADS domain | ~4 e | ~2 c | ~1 d |
| HSF family | ~5 e | ~1 c | $\sim 1d$ |

Table Legend. Major Classes of Eukaryotic DNA Binding Proteins. The number of proteins containing the specified Pfam domains as well as the total number of domains (in parentheses) are shown in each column. Unless otherwise indicated, Celera data (Venter et al., Science, 2001) were used; Celera data were used instead of the Public Consortium data because the Celera data provided values for a greater number of different types of DNA binding domains. (a) indicates data from Newman and Keating, Science, 2003. (b) indicates data from Fassler et al., Genome Res., 2002. (c) indicates data from a polypeptide search of FlyBase. (d) indicates a search of SGD. (e) indicates data on known gene names and descriptions from a gene family search at the UCSC web browser.

In order to evaluate the general applicability of our compact combinatorial DNA microarrays in determining transcription factor (TF) binding sites, we have selected ~50 transcription factors (TFs) from *S. cerevisiae* and *D. melanogaster* that they span a variety of structural classes of DNA binding domains (DBDs) found in eukaryotes. These proteins can be evaluated using a compact DNA array.

Example 2

Design and Simulations of the Microarrays of Compact Combinatorial DNA

The following is one implementation for providing a collection of sequence in which all possible DNA sequence variants can be represented on DNA microarrays in a space- and cost-efficient manner. One advantage of this technology is that only a minimal number of individual DNA sequences and individual DNA spots needs to be synthesized. All possible binding sites (which we term k-mers) are represented in an efficient manner by allowing distinct, non-similar sites to overlap with each other on a given DNA fragment. Of course, less than all possible sites can also be used. For example, it is possible to exclude homopolymer tracts of length k, k-1, or k-2, or to omit other simple sequences, e.g., tracts of length k, k-1, or k-2 that include only two types of nucleotides.

Typically, the DNAs are significantly longer than k. The addition of each base to the length of the oligonucleotide ('oligo') adds another k-mer to that oligo. Compared to the use of a single k-mer per oligo, this approach reduces the number of oligos required to interrogate a set of proteins to discover their DNA binding site sequence interaction preferences.

One or more of the factors can be included in the design of such DNA sequences: 1) placing all possible or a significant percentage of all (e.g., at least 60, 70, 80, 85, 90, 95, 98, or 99%) DNA binding sites within a given binding space (termed a 'Hamming ball'; here, a 'Hamming ball' refers to a most preferential DNA binding site plus all DNA sequences that are within an arbitrary number of mismatches from it) to be located on separate double-stranded oligos and/or separate DNA spots on a DNA microarray; 2) including multiple copies of a given DNA k-mer, with each copy flanked by unique flanking sequence so as to take into account potential junction effects; 3) positioning a given k-mer, if it is located at one end of a double-stranded DNA oligo, at a different location, e.g., centrally within or at the other end of a different double-stranded DNA oligo at another spot on the DNA microarray so as to take into account possible steric effects of the slide surface and/or the requirement for flanking DNA sequence; 4) taking into account in the array design that k-mers within a given Hamming ball might be found on either strand (forward or reverse complement) of double-stranded DNA oligos.

There are a number of possible ways to design such a set of DNA sequences. We have calculated a maximally compact representation of all possible binding sites (binding sites). Using a standard tool from cryptography called a linear shift register, we were able to construct in silico an appropriate long sequence that contains all words of a given length exactly once. See, e.g., S. Golomb, Shift Register Sequences, Aegean Park Press, 1967. Other methods for constructing a string that contains all words (or a substantial fraction of all, e.g., at least 70, 80, 85, 90, 95, 98, 99% of all words) of a given length can also be used.

This long sequence is segmented into short sequences of the same length with overlapping ends to ensure that none of the k-mers contained within it is destroyed in the segmenting process. These shorter sequences correspond to the individual spots on our combinatorial microarrays. In this implementation, each of our two shift registers represents each 9-mer once. Because a given k-mer and its reverse complement should be bound equally well by a given agent, our two shift registers will have every 9-mer represented four times. Similarly, each 8-mer can be represented 16 times, each 7-mer 64 times, and so on.

In evaluating interaction with an array, first, it is helpful to provide a means of discerning which of the words contained within a 'bound' spot are actually binding sites. This ensures that one can assay the relative binding affinity of the agent for each of the different candidate binding sites. We refer to the array design criterion of insuring that as few distinct k-mers as possible within a given molecule are recognized by a given agent as "discernability."

Second, it is helpful to provide a way of recovering which k-mer in a molecule is recognized by the agent. We refer to identifying the relevant k-mer from other k-mers present in the same molecule as "recoverability." In some cases, there can be more than one recognized k-mer per spot, and the observed signal would presumably be due to some combination of the affinities of the TF for each of these sites. Further characterization (e.g., EMSA, footprinting, mutational analysis) can be used to identify such situations.

We have formalized the notions of: 1) 'discernability', e.g., ensuring that for every 'Hamming ball', for each of its words there exists at least one spot that does not contain another word from that Hamming ball, and 2) 'recoverability' of Hamming balls. These two concepts (discernability and recoverability) jointly facilitate determining which particular k-mer is actually bound in a molecule. We assume that for any agent whose binding site is of length k, most of the high affinity binding sites can be within a given number r of mismatches of some central word w or its reverse complement (simplistically one could think of this central word as the 'consensus'). We refer to the collection of all words within r mismatches of w as a "ball of radius r and centered at w," or simply $B(w,r)$. In the following calculations, we found which ball contains the binding sites from the collection of 'bound' spots, thus solving the recoverability problem. Furthermore, we show that for any word w' in a ball $B(w,r)$ there will almost always exist at least one spot were w' occurs in the absence of any other word from $B(w,r)$, thus solving the discernability problem. Here, we considered binding sites with widths of lengths 6 through 9, and have assumed that their binding sites are contained within balls of radius 1 or 2 (in the case of k=9 we also looked at a radius of 3); e.g., for all words of length 6, 7, or 8, we considered all possible single and double mismatches, and for words of length 9, we also considered all possible triple mismatches.

In one exemplary design, oligonucleotides that are 60 nucleotides in length are used. A 60 nucleotide oligonucleotide can include a 16 nt universal primer sequence incorporated at the 5' end of each oligo. In addition, we have chosen to incorporate 5 N's (where N=A/C/G/T) between the universal primer sequence and the combinatorial portion of the sequence so as to minimize any possible artifactual binding due to junction effects between the universal primer sequence and the combinatorial portion of the sequence. We have also chosen to incorporate 5 N's flanking the other end of the combinatorial portion of the sequence so that the combinatorial portion of the sequence is not at the very terminus of the DNA, since many DNA binding proteins need to make non-specific contacts with DNA beyond nucleotides with which it makes sequence-specific contacts. Therefore we are left with just 34 by for the combinatorial portion of each oligo. For binding sites 9 by in length, the internal 34 by will contain 34−9+1=26 potential binding sites. Given these constraints, a DNA microarray with 20,166 spots would contain two shift registers, and thus would contain each 9-mer four times (when reverse complements are considered). Spotting this number of spots onto a standard 1×3 inch glass slide format can readily be achieved using standard robotic arraying instruments.

Provided in the Table below is an exemplary listing of how many times a given k-mer (a "word") can be represented in a shift register designed to contain all possible k-mers:

|  |  | shift register size (e.g., designed for what k-mer) | | | | | | |
|---|---|---|---|---|---|---|---|---|
|  |  | 6 | 7 | 8 | 9 | 10 | 11 | 12 |
| k-mer | 6 | 2 | 8 | 32 | 128 | 512 | 2048 | 8192 |
| (e.g., "word" | 7 |  | 2 | 8 | 32 | 128 | 512 | 2048 |
| length) | 8 |  |  | 2 | 8 | 32 | 128 | 512 |
|  | 9 |  |  |  | 2 | 8 | 32 | 128 |
|  | 10 |  |  |  |  | 2 | 8 | 32 |
|  | 11 |  |  |  |  |  | 2 | 8 |
|  | 12 |  |  |  |  |  |  | 2 |

Provided in the Table below is an exemplary listing of how many spots on a microarray would be required to represent a given shift register size (e.g., designed for what k-mer), using 2 different permissible combinatorial sequence lengths (44 nt, which corresponds to a 60-mer minus a 16 nt universal primer sequence; 34 nt, which corresponds to a 60-mer minus a 16 nt universal primer sequence, minus 5 degenerate ("N") positions on either side of 34 combinatorial positions) as examples:

| register size | # combinatorial positions = 44 #spots required | # combinatorial positions = 34 #spots required |
|---|---|---|
| 6 | 106 | 142 |
| 7 | 432 | 586 |
| 8 | 1772 | 2428 |
| 9 | 7282 | 10083 |
| 10 | 29960 | 41944 |
| 11 | 123362 | 174763 |
| 12 | 508401 | 729445 |

Note that up to 30,000 spots, thus shift registers designed for up to 10-mers in the case of spots containing 44 combinatorial positions, and shift registers designed for up to 9-mers in the case of spots containing 34 combinatorial positions, can be easily printed onto standard size 1 in×3 in glass slides using typical microarray printing robotic instruments.

We have run computational simulations on our compact combinatorial array design; the results of these simulations indicate that almost all words in almost all Hamming balls are discernable, and that it is unlikely for a Hamming ball to be unrecoverable. Any possible DNA binding site can be extracted from such 'combinatorial arrays.' The arrays can be used to distinguish between two very similar DNA binding sites. For discernability, we worked under the 'worst case' assumption that all words within the ball were binding sites; this can be considered 'worst case' since the larger the number of binding sites, the harder it is to distribute them on the array in a fashion so that two binding sites do not occur on the same spot. For each k, we considered all balls of radius r For each ball, we determined whether each word in the ball occurred at least once on a spot in the absence of any other word in the ball. For that ball, we then computed the proportion of words that were discernable under the assumption that all words in the ball could be binding sites. Reported below are the average values of the proportion of words in the ball centered at w that were discernable, across all balls for $6 \leq k \leq 9$:

k=6, r=1: average discernability=99.998% k=6, r=2: average discernability=99.790% k=7, r=1: average discernability=99.995% k=7, r=2: average discernability=99.803% k=8, r=1: average discernability=99.997% k=8, r=2: average discernability=99.897% k=9, r=1: average discernability=99.954% k=9, r=2: average discernability=99.474% k=9, r=3: average discernability=81.578%

Thus, we see that almost all binding sites are discernable for all k and all r that we considered (for candidate binding sites of length 6, 7, or 8, we considered all possible single and double mismatches, and for candidate binding sites of length 9, we also considered all possible triple mismatches). Similar simulations can be used to evaluate properties of Hamming balls of size B(6,3), B(7,3), B(8,3), B(8,4), and B(9,4).

To test the expected recoverability rate, we developed a simulator that first picks a ball B of a given radius r surrounding a given randomly chosen word. The program then picks a random collection of words within the ball to be considered binding sites and marks the spots containing these words as 'bound.' The program then asks if there is another possible subset of words from some ball that could have caused the exact same collection of spots to be 'bound'. Because there are $4^k$ balls for each k, and because for each candidate ball all of its subsets must be examined, one is limited for practical reasons in the number of simulations that can be performed. Therefore, for each $6 \leq k \leq 9$ and each r equal to 1 or 2 (or 3 for k=9), we generated 500 collections of binding sites, and then checked each collection to see if the ball containing these sites was recoverable.

Out of all 9 of these sets of 500 collections of binding sites, the ball containing the binding sites was always recoverable. Moreover, even if the binding sites are not recoverable, it appears to be very likely that the binding sites would always be contained within one of a very limited number of candidate balls, and the correct one could then be identified, e.g., with a small set of EMSAs.

Furthermore, we wanted to rigorously test the hypothesis that the collection of binding sites for a given agent can be contained within a Hamming ball of a given width and radius. In other words, we wanted to ensure that most transcription factor DNA binding sites were of a length and sequence degeneracy that would allow us to extract PBM data on each of their individual candidate binding sites using our combinatorial arrays.

We extracted transcription factor binding site data from the TRANSFAC database for 110 non-redundant TFs (fungi, 1; insect, 8; plant, 12; vertebrate, 91) for which in vitro binding site selection (SELEX) data was available. For each of these TFs we then generated the corresponding binding site motifs. We generated a matrix P(i,j) to represent the frequency of nucleotide i at position j of each TFs' binding site motif. Next, we assumed a background mononucleotide frequency of A or T=0.28 and G or C=0.22 (this is very close to the nucleotide frequencies within 50 kb upstream of transcriptional start and downstream of transcriptional stop for the human, mouse and fly genomes). We shall use Q to denote this background probability distribution on {A,C,G,T}. At each position j, we sought to compare the distribution of nucleotides P(i,j) to the background distribution Q(i). If P(i) was 'far' from Q(i) at position j, then we considered position j to be part of the binding site motif, while if P(i) was very close to Q(i) for a given j, then we did not consider it to be part of the binding site motif. However, such a calculation required a definition of distance, as well as a concept of the average distance that any randomly selected distribution P(i,j) is from Q(i,j). For the metric, we chose to use relative entropy, which we denote by R. Here, if P and P' are any two probability distributions, then their relative entropy is given by:

$$R(P, P') = \sum_{i \in \{A,C,G,T\}} P(i) \log\left(\frac{P(i)}{P'(i)}\right)$$

We computed the average 'distance' of a generic probability distribution P from Q by integrating R(P,Q) over all possible probability distributions P (this was done numerically via a Monte Carlo simulation). We let µ denote the result of this integral (approximately equal to 0.18). For a given TF and a given input width of binding site, we took the frequency matrix P(i,j) and the background distribution and computed the sum:

$$S = \sum_j (R(P(i, j), Q) - \mu)$$

Because the term R(P(i,j),Q)–µ has mean zero and is positive if P(i,j) is close to Q and negative if it is far, we can take the width of the motif to be the value that maximizes the quantity S. We performed this calculation for all 109 transcription factors for which binding site data from SELEX experiments was available in TRANSFAC. For those transcription factors whose binding site motif widths were 13 by or shorter, we computed the radius of the Hamming ball that contained them. The results of these calculations, combined with the simulations described above for various Hamming balls, indicate that our combinatorial arrays will allow us to discern the relative binding preferences for most transcription factors whose DNA binding sites are 9 by or fewer.

We have found that the DNA binding site motifs that we have identified using PBM technology can correspond well to the DNA binding site motifs we determined from an analysis of the genome-wide location analyses (ChIP-chip) performed by Lee et al. on these same transcription factors. Lee et al.: Transcriptional regulatory networks in *Saccharomyces cerevisiae*. Science 2002, 298:799-804.

Synthesis of the Compact Combinatorial dsDNA Microarrays:

Double-stranded DNAs (dsDNAs) 60 by in length can be synthesized as described previously in Bulyk et al. (2001) Exploring the DNA-binding specificities of zinc fingers with DNA microarrays. Proc. Natl. Acad. Sci. U.S.A. 98:7158-7163. Briefly, oligos 60 by in length can be synthesized (Illumina) such that they contain our compact combinatorial DNA design plus a universal primer sequence 16 by in length. Two different universal primer sequences can be used, so as to allow us to identify and control for any specific binding either to a site within one of the universal primers or a site resulting from the junction of the universal primer sequence with the variable (compact combinatorial design) region. These two different universal primers were designed to represent as different as possible a set of k-mers, so as to ensure that in case one of the universal primers happened to contain a binding site for a TF, that the other one probably would not also contain a binding site for that TF. Moreover we have designed two independent, complete sets of compact combinatorial DNAs, and each one of these can be used with a different one of the two universal primers, so that in the end there are a total of two unique sets of universal primer+compact combinatorial DNAs. Each full-length oligo can be combined with its universal primer in a 2:1 molar ratio in a primer extension reaction in a 96-well plate format employing the SEQUENASE™ V2.0 DNA polymerase (United States Biochemical). The completed primer extension reactions can be purified away from the unincorporated universal primer and dNTPs and exchanged into printing buffer by using QIAQUICK™ filtration plates (Qiagen). Purified dsDNAs can be replicated into 5 daughter plates which can be used for printing the microarrays.

Before synthesizing the full set of compact combinatorial DNAs, we will first compare two different methods for attachment of dsDNAs to glass slides, with regard to the quality of the resulting PBM data. In the first method, the dsDNAs are end-attached to amine-reactive slides through the use of amino-tagged universal primers, as described previously. Alternatively, unmodified dsDNAs can be spotted onto GAPS II™ slides (Corning), and then covalently attached to the slides via UV-crosslinking. Specifically, the microarrays can be rehydrated and then UV-crosslinked in a STRATALINKER™ (Stratagene). End-attachment of the dsDNAs should allow the DNAs to not be kinked and to be maximally accessible for interaction with DNA binding proteins. However, the use of unmodified dsDNAs would allow us to use GAPS II™ slides instead of amine-reactive slides which are extremely moisture-sensitive. It is possible that a UV-crosslinking method could be developed that would optimize the two opposing issues of: (1) ensuring that the DNA structure is as unperturbed as possible, e.g., ideally most DNA molecules will have just one crosslink to the slide surface; (2) ensuring that most spotted DNA molecules can be attached to the slides.

TF Cloning, Expression, and Purification:

We have successfully used TFs epitope-tagged with the FLAG tag and separately with GST in PBM experiments. The epitope tag serves a dual purpose; it allows for both purification and labeling with a respective fluorophore-conjugated anti-tag antibody (such as Alexa488-conjugated anti-GST antibody). *E. coli* is a robust, convenient, and inexpensive expression system for the production and purification of epitope-tagged human proteins, including TFs. Braun et al. Proc. Natl. Acad. Sci. U.S.A. 2002, 99:2654-2659. DNA binding proteins can be cloned into GATEWAY™ (Invitrogen) entry clones and then transferred into GATEWAY™ compatible expression vectors. After complete sequence verification of the entry clones, the genes can be moved into the pDEST15 expression vector, which provides an N-terminal GST fusion tag. Subcloning of these genes can be performed by using standard GATEWAY™ recombinational subcloning methodology. High efficiency competent cells of DH5alpha and BL21(DE3)pLysS strains of *E. coli* can be used for transformations. Expression is preferably in BL21(DE3)pLysS; alternatively, fusion proteins can be expressed in yeast or insect cells, or by in vitro transcription and in vitro translation using either an *E. coli* lysate system or a rabbit reticulocyte lysate system (see below). Proteins can be expressed, for example, as full length proteins or as fragments, e.g., a fragment that includes the DNA binding domains. Since many known and predicted yeast and fly TFs are fairly large (>80 kDa), we may have to express and purify just the DNA binding domains of a number of these TFs.

Proteins expressed in *E. coli* can be tested for solubility and purity by denaturing gel electrophoresis. It is expected that all the expressed proteins may not be obtained in the soluble fraction in our initial expression attempts. Induction at lower temperature (18° C.) can be attempted for proteins which are not obtained in the soluble fraction. Slower growth of bacterial cells leads to lower expression levels of the over-expressed protein, which may alleviate aggregation of the expressed protein into inclusion bodies and help us to obtain a greater percentage of the protein in the soluble fraction. Conditions such as the use of lower concentrations of IPTG will also be tested. Should protein solubility be an issue, it is possible to modify purification protocols by using detergents or by using different bacterial strains. Use of mutant bacterial strains for expressing fastidious proteins has been reported previously. See, e.g., Miroux et al. J. Mol. Biol. 1996, 260: 289-298. Purification of the GST-fusion proteins can be performed according to standard protocols. Briefly, GST-fusion protein can be bound to glutathione agarose beads, washed, and then eluted with reduced glutathione.

It is also possible to produce the proteins in vitro, e.g., using a cell-free E. coli extract. In vitro translation can be performed, e.g., in microtitre wells, or even directly on an array, e.g., for high throughput screening purposes. After translation, the entire array can be washed to remove the translation extract and unbound protein.

Protein Binding Microarray (PBM) Experiments and Data Analysis:

Protein binding reactions and subsequent labeling can be performed essentially as described in Preliminary Studies. Before synthesizing the two unique sets of compact combinatorial DNAs, we will first synthesize just one set (with just one universal primer sequence), so as to determine how well we can extract TFBS motifs from the combinatorial array PBM data. PBM experiments and SYBRGREEN™ I (SGI) staining of the combinatorial dsDNA microarrays can be performed in triplicate. All microarrays used for a given TF can be from the same print run, so as to minimize variation. We typically scan the labeled, protein-bound microarrays and the SGI-stained microarrays not just once but rather multiple times, at a range of different laser power intensities (or PMT gain settings). We typically scan at ~3-6 different laser power intensities (or PMT gain settings) per microarray; this allows us to capture signal intensities for even very low signal intensity spots, while ensuring that we capture sub-saturation signal intensities for each of the spots on the microarray. Microarray TIF images can be quantified with GENEPIX™ microarray analysis software. Background-subtracted median intensities can be calculated using the median local background surrounding each spot, in order to account for uneven distribution of background fluorescence over the slide surface. We can use MASLINER™ (MicroArray Spot LINEar Regression) software to calculate the relative signal intensities over all the laser power (or PMT gain) settings in a semi-automated fashion. Specifically, MASLINER™ combines the linear ranges of multiple scans from different scanner sensitivity settings onto an extended linear scale. Dudley et al. Proc. Natl. Acad. Sci. U.S.A. 2002, 99:7554-7559. We can calculate the fractional signal intensity of each spot, relative to the total signal intensity on the microarray. To control for variation in DNA concentration, we normalize each spot's PBM fractional signal intensity by its SGI fractional signal intensity.

The data from these PBM experiments using the compact combinatorial DNA microarrays can be analyzed essentially the same way as we currently analyze our yeast intergenic microarray PBM data. Briefly, after running MASLINER™ on multiple scans, the microarray data can be filtered so that only data from high quality spots are retained. To achieve this, a number of criteria can be applied to ensure that only high quality spots can be analyzed. First, for each of the triplicate microarrays, data corresponding to any spots that are flagged "Bad" (e.g., dust flecks, etc.) can be removed. Data from each of three triplicate microarrays can be normalized according to total signal intensity, so that the average spot intensity is the same for all three slides. Then, within each individual slide, the data can be separated into sectors, e.g., according to their local region on the slide. In one example, we have organized the spots into the 32 subgrids of the printed microarray. The data will then be normalized again so that the average spot intensity is the same over all the sectors; this serves to normalize for any region-specific non-homogeneity in the background and also binding and labeling reactions. Any spots with SD/median greater than 2.0, e.g., spots with highly variable pixel signal intensities, can be filtered out. The background-subtracted, normalized signal intensities for all spots with reliable data in at least two of the three replicate microarray experiments can be averaged, and the SD/mean can be calculated. The SGI microarray data are treated exactly the same way, except that any spots with fewer than 50% pixels with signal intensities greater than (median background intensity+2 SDs) are also filtered out, as these spots presumably do not have enough DNA present to be able to measure accurate signal intensities.

For each spot, we calculate ln (mean PBM/mean SGI) and create a scatter plot of the log ratio versus the spots' SGI intensities. Although we expect that the log ratio should be independent of DNA concentration, we have found that higher concentrations, as determined by higher SGI signal intensities, seem to exhibit proportionately less bound protein. In order to restore the independence of log ratio and SGI intensity, the scatter plot is fit with a locally weighted least squares regression using the LOWESS function of the R statistics package (smoothing parameter=0.5). We subtract the value of the regression at each spot from its log ratio, yielding a modified log ratio that is independent of DNA concentration. We then plot the distribution of all log ratios as a histogram (bin size=0.04), which resembles a Gaussian with a heavy tail. We determine the mode of the distribution by searching for the window of five bins with the highest number of spots and taking the middle bin. We then reflect all values less than the mode and fit these values to a Gaussian function using the MATHEMATICA™ software package (Wolfram Research, Inc.). This gives the mean and standard deviation (SD) of the distribution. We adjust all log ratios so that the peak is centered on zero. We then calculate a p-value for each individual spot based on the number of SDs its log ratio is above the mean of the Gaussian distribution. In order to correct for multiple hypothesis testing, all individual p-values are then adjusted to a modified significance level using a modified Bonferroni correction.

Example

The appendices filed in U.S. Ser. No. 60/587,066 provide four actual examples of sequence sets for combinatorial arrays. Each set represents a complete design, either for an all 9-mer design (k=9) or an all 8-mer design (k=8). We can readily create all k-mer designs for any word (e.g., binding site) length k.

Arrays can be printed which include these sequence sets. Oligonucleotides for the arrays can further include an invariant sequence, such as an appended universal primer sequence, each 16 nt long, to each of the 5' ends of each of these sequences. The invariant sequence can be used for subsequent primer extension to create double-stranded DNAs from the single stranded oligonucleotide template. Examples of primers sequences that could be used include: TCAAGTCAATCGGTCC (SEQ ID NO:1), ATCGCAGTTAGCAATG (SEQ ID NO:2), and GGGTAGAGGGTTTCAA (SEQ ID NO:3).

Example

A nucleic acid array was prepared using a set of oligonucleotides that cover all 8-mers (k=8). The oligonucleotides have a total sequence length of 60. These sixty nucleotides include:

9 nucleotides as "linker" sequence that that spaces the universal priming sequence from the slide surface (various sequences can be used, in this example use 9 T's);

24 nucleotides as the universal priming sequence;

27 nucleotides as the combinatorial sequence.

With this arrangement, one array for all 8mer was covered by 3277 spots. The array was made double stranded using a primer. Synthesis of the second strand from the primer was confirmed on one array by incorporation of ALEXA®488-dUTP. Primer binding could also be confirmed using a Cy5-labelled primer (24 nucleotides in length).

Protein binding to an array of this design was evaluated using an ALEXA®488-labeled anti-GST antibody as follows. The yeast transcription factor CBF was expressed as a GST fusion protein and bound to the double-stranded array. Location of the protein was detected using the ALEXA®488-labelled anti-GST antibody. Imaging of the array indicated that only particular locations were bound by the CBF protein. An analysis of the ten brightest spots indicated the presence of binding sites that match well to the known CBF binding site.

Example

We have developed a new DNA microarray-based in vitro technology, termed protein binding microarrays (PBMs), that allows rapid, high-throughput characterization of the DNA binding site sequence specificities of transcription factors in a single day. Using PBMs, we identified the DNA binding site sequence specificities of the yeast transcription factors Abf1, Rap1, and Mig1. Comparison of these proteins' in vitro binding sites versus their in vivo binding sites indicates that PBM-derived sequence specificities can accurately reflect in vivo DNA sequence specificities. In addition to previously identified targets, Abf1, Rap1, and Mig1 targeted about 100, 90, and 70 new target intergenic regions, respectively, many of which were upstream of previously uncharacterized open reading frames (ORFs). Comparative sequence analysis indicates that many of these newly identified sites are highly conserved across all five sequenced sensu stricto yeast species and thus are likely to be functional in vivo binding sites that potentially are utilized in a condition-specific manner. Similar PBM experiments will likely be useful in identifying cis regulatory elements and transcriptional regulatory networks in various genomes.

The ability of an organism to adapt to its environment, respond to extracellular cues, and perform vital cellular functions requires the specific and coordinated expression of thousands of genes. The interactions between transcription factors (TFs) and their DNA binding sites are an integral part of their transcriptional regulatory networks. These interactions control critical steps during normal growth and in response to external stimuli. For yeast, although the genomes of several different species have been sequenced and analyzed[1,2], much still remains to be understood about how yeast genes are regulated. Significant progress has been made recently in the accumulation and analysis of mRNA transcript profiles[3,4], locations of in vivo binding sites of TFs[5-8], and protein-protein interactions[9-12]. However, there are still many TFs whose DNA binding specificities and regulatory roles are unknown.

Protein binding microarray (PBM) technology allows the in vitro binding specificities of TFs to be determined in a single day by assaying the sequence-specific binding of TFs directly to double-stranded DNA microarrays spotted with a large number of potential DNA binding sites. A DNA binding protein of interest (e.g., a yeast TF) is expressed with an epitope tag, purified, and then bound directly to a double-stranded DNA microarray (here, a whole-genome yeast intergenic microarray). The protein-bound microarray is then washed gently to remove any nonspecifically bound protein, and labeled with a fluorophore-conjugated antibody that is specific for the epitope tag.

Binding site data from PBMs on yeast TFs corresponded well with binding site specificities determined from ChIP-chip. Moreover, comparative sequence analysis of the PBM-derived binding sites in *S. cerevisiae* with those in the orthologous positions in the sequence alignments of *S. mikatae, S. kudriavzevii, S. bayanus*, and *S. paradoxus* indicated that many of the sites bound in PBMs, including some not identified by ChIP-chip, are highly conserved and thus are likely to be functional in vivo binding sites that potentially are utilized in a condition-specific manner. Since there are many known TFs and predicted DNA binding proteins whose DNA binding specificities have not been characterized, our PBM technology will likely aid in the annotation of many regulatory proteins and DNA sequence motifs, and it may allow them to be connected to one another and to gene regulatory networks.

Results

Protein Binding Microarray Experiments

As a validation of this approach, we bound CBP-FLAG-Rpn4 fusion protein to microarrays spotted with a number of positive and negative control spots for binding by Rpn4. We labeled the protein-bound array with Cy3-conjugated M2 anti-FLAG primary antibody (Sigma), and scanned it with a microarray scanner (GSI Lumonics SCANARRAY™). Only the spots that contain good matches to the binding site motif for Rpn4 exhibit high signal intensity. As we previously found that higher signal intensity is in general indicative of higher DNA-protein binding affinity[14], this CBP-FLAG-Rpn4 PBM indicates that our new PBM technology is successful in identifying sequence-specific TF binding.

We applied the PBM technology on a genome-wide scale by using whole-genome yeast intergenic arrays in PBM experiments to identify the sequence specificities and target genes of three yeast TFs: ARS-binding factor 1 (Abf1), repressor-activator protein 1 (Rap1), and Mig1. Abf1 has a CHC2 zinc finger DNA binding domain, binds origins of replication, and is a transcriptional silencer[20]. Interestingly, binding of Abf1 induces a DNA bend of approximately 120°[21]. Rap1 binds to DNA via a Myb-like helix-turn-helix DNA binding domain and, among other roles, regulates telomere length and expression at the silent mating-type loci HML and HMR[22]. Mig1 has two C2H2 zinc fingers in its DNA binding domain, and it is involved in the repression of glucose-repressed genes[23].

The whole-genome yeast intergenic arrays were spotted with essentially all of the known intergenic regions in the yeast genome[5]; the lengths of the 6723 unique spotted PCR products ranged from ~60 to ~1500 bp, with an average length of ~480 bp. We used Abf1, Rap1, and Mig1, dually-tagged at the N-terminus with glutathione S-transferase (GST) and $His_6$, in PBM experiments using these microarrays. The washed, protein-bound microarrays were labeled with Alexa 488-conjugated anti(GST) antibody (see Methods), and then scanned with a microarray scanner. The microarray TIF images were quantified using GenePix Pro version 3.0 software (Axon Instruments, Inc.) (see Methods). In one case, a whole-genome yeast intergenic microarray was used in a PBM experiment with the yeast TF Rap1. Negative control PBMs performed on recombinant GST (Sigma) and GST-$His_6$ purified from yeast did not result in sequence specific DNA binding, indicating that there is no specific DNA binding conferred by these epitope tags. In addition, we performed negative control PBMs with calmodulin (Cmd1), which is not a DNA binding protein. As expected, the GST-$His_6$-Cmd1 PBMs also did not show evidence of sequence specific DNA binding. Thus, we expect sequence-specific binding in our PBM experiments only from sequence-specific DNA binding proteins. For each TF, the experiments were performed in triplicate. We found that the PBM data are highly reproducible, with most spots having SD/mean values less than 0.3. In general, the spots with the greatest variation are the ones with the lowest signal intensities, and thus were least likely to enter into our motif finding analysis.

In order to allow for the normalization of the PBM data by relative DNA concentration, we stained separate microarrays from the same microarray print run with SYBRGREEN™ I (Molecular Probes), which is specific for double-stranded DNA. Normalization by relative DNA concentration is important, since there can be significant variation in the amount of DNA present in each spot due to variation in the concentration of the DNAs that are spotted. We evaluated the distribution of the log ratios of mean PBM to mean SYBRGREEN™ I signal intensities for the set of triplicate Rap1 PBM experiments. We interpret the distribution of spots on the left, which is fit well by a Gaussian, to correspond to the spots that are bound nonspecifically. Conversely, we interpret the heavy upper tail of the distribution to correspond to spots bound specifically by the TF. For each spot we calculate a p-value for specific binding based on the number of standard deviations the spot's log ratio was above the mean of the Gaussian distribution, taking into account the width of that distribution (see Methods).

We applied the Modified Bonferroni Method to correct for multiple hypothesis testing in order to further increase our confidence in what we identify as 'bound' spots. We determined the numbers of unique spots that pass a 0.05, 0.01, or 0.001 p-value threshold for the PBM data of Abf1, Rap1, or Mig1. We have used a stringent p-value threshold of 0.001 even though we anticipate that it may increase our false negative rate, so as to increase the likelihood that spots passing our p-value threshold correspond to true positives. The spots with high log ratio PBM data correspond to the intergenic regions upstream of RPL14A, RPL8A, and OP13, all of which are known to be direct targets of Rap1.

Identification of DNA Binding Site Motifs

We expected to be able to determine the DNA binding site specificity of a TF from analysis of the sequences with the highest PBM/SYBRGREEN™ I log ratios. We analyzed the sequences corresponding to those spots with a Bonferroni-corrected p-value of less than 0.001 with the motif discovery program BioProspector[24] in order to identify the TF's DNA binding site motif. Analysis of these sequences for over-represented DNA sequence motifs produced the Rap1, Abf1, and Mig1 binding site motifs. As can be seen, the PBM technology allows the identification of both ungapped (e.g., Rap1 and Mig1) and gapped (e.g., Abf1) DNA binding site motifs. Moreover, we were able to derive the binding site motif for Mig1 from the PBM data, whereas analysis of ChIP-chip data[8] did not result in the Mig1 binding site motif. The group specificity score[25,26] (see Methods) for each of the PBM motifs ($p=1.1 \times 10^{-222}$ for Rap1; $p=1.7 \times 10^{-151}$ for Abf1; $p=1.4 \times 10^{-65}$ for Mig1) was also evaluated. Compared to the corresponding computational negative controls on matched sets of randomly selected intergenic regions (see Methods), the group specificity scores derived from the PBM data for each of these three TFs are extremely significant. Thus, we have confidence that the PBM data represent true sequence-specific binding of TFs to their DNA binding sites.

The PBM data are based on an assay of all possible binding sites in the noncoding portion of the S. cerevisiae genome. To confirm and further explore the high resolution binding site data generated from PBMs, we performed electrophoretic mobility shift assays (EMSAs). EMSAs involving an intergenic region that was bound significantly by Rap1 in PBMs indicated the superiority of the PBM motif over the TRANSFAC motif in identifying high affinity TF binding sites. Specifically, the intergenic region iYPL221W contained a highly significant match (GGTGCACGGATT) to the Rap1 binding site motif and scored significantly in PBMs ($p=3.9 \times 10^{-21}$), but it was a poor match to the TRANSFAC™ Rap1 motif. Use of the TRANSFAC™ motif would predict the underlined nucleotides to be unfavorable for Rap1 binding, whereas these nucleotides are tolerated in the PBM motif. Our EMSA analysis of the sequence consisting of this Rap1 binding site, flanked by its native intergenic sequence, indicated that Rap1 is capable of high affinity binding to this sequence. This is an example of a high affinity TF binding site.

To approximate the potential false positive rate from PBMs, we determined the fraction of spots passing a 0.001 p-value threshold that were not identified by BIOPROSPECTOR™[24] as containing a sequence belonging to the given TF's binding site motif. This is by no means a perfect measure; for example, some of these potential false positives could simply have either weaker matches to the identified motif or perhaps have multiple occurrences of lower affinity sites that were not identified by the motif finder as belonging to the motif that represents the majority of the identified binding sites. For example, the intergenic region iYLL051C, which passed the 0.001 p-value threshold but had only a weak sequence match to the Rap1 PBM motif, was confirmed by EMSAs to be bound by Rap1 in vitro. This finding indicates that some intergenic regions may contain high affinity binding sites that are not strong sequence matches to the given TF binding site motif Thus, it is possible that the false positive rate is lower than the one we have estimated. Nevertheless, using this approximate measure of false positives, we found that our false positive rates ranged from approximately 7% to 9% of 'bound' spots. Importantly, for all three TFs, a much larger number of potentially real binding sites was identified from the PBM data as compared to the number identified from ChIP-chip experiments.

Comparison of PBM Data Versus Chromatin Immunoprecipitation Data

DNA binding site motifs identified with the PBM technology for Abf1 and Rap1 corresponded well to motifs determined from analysis of ChIP-chip data passing a $10^{-3}$ p-value threshold for these same TFs[7,8]. The group specificity score[25,26] for each of the ChIP-chip motifs was less significant than was the group specificity score for the respective PBM motifs, indicating that not all binding site sequence matches were identified as bound in the ChIP-chip experiments. Venn diagrams were used to compare the PBM data for Rap1, Abf1, and Mig1, respectively, with the ChIP-chip data for these same TFs[7,8]. Of the ~6400, ~6100, and ~6400 unique intergenic PCR products that passed our various PBM data quality control filters for Rap1, Abf1, and Mig1, respectively, previously published ChIP-chip data[7,8] was also available for 99.9%, 93.1%, and 93.7% of these intergenic regions. For both Rap1 and Abf1, the intergenic regions identified as bound by PBMs overlapped with a majority of the regions identified as bound by ChIP-chip, while certain intergenic regions were identified as bound either just by PBMs or just by ChIP-chip. Unlike for Rap1 and Abf1, the intergenic regions identified as bound by Mig1 in PBMs overlapped with only a small number of the regions identified as bound by ChIP-chip. Furthermore, many fewer regions were identified as bound in ChIP-chip as compared to PBMs. Since Mig1 is known to be regulated at the level of nuclear localization[23], it is possible that the yeast cultures for the ChIP-chip experiments were such that Mig1 may have been predominantly cytoplasmic. Thus, in addition to previously identified targets, we have identified 103, 86, and 69 new target intergenic regions for Abf1, Rap1, and Mig1, including those upstream of 25, 40, and 29 previously uncharacterized open reading frames (ORFs), respectively.

There are many biological reasons why certain intergenic regions would be bound either only in vitro or only in vivo. For example, a trans-acting factor adjacent to a TF binding site could prevent a TF from binding in vivo, or local chromatin structure could provide a non-permissive environment for binding. Conversely, a TF could indirectly interact with a particular intergenic region in vivo, in the absence of its own DNA binding site, through protein-protein interactions. In order to attempt to find evidence for such co-regulatory mechanisms, for each TF we searched each of these sets of intergenic regions for secondary DNA sequence motifs that might be involved in such co-regulation. A secondary motif specific for the regions bound only in vivo might correspond to a binding site for either a protein cofactor or a recruiting protein that allows the target TF to contact the DNA through an indirect interaction. Alternatively, a secondary motif specific for the regions bound only in vitro might correspond to a binding site for a separate factor that blocks access to these DNA binding sites under the conditions in which the yeast cultures were grown for the ChIP-chip experiments. We did not find any secondary motifs that achieved statistical significance, potentially because of the abundance of different modes by which binding of TFs to DNA is regulated in vivo. However, it is possible that such secondary motifs might exist for TFs not studied here.

Conservation of Identified Binding Sites Across All Five Sensu Stricto Yeast Genomes To find evidence supporting our hypothesis that the regions bound only in vitro are functional in vivo but for some specific biological reason have not been identified previously as bound, we mapped the predicted binding sites in *S. cerevisiae* to the orthologous positions in the sequence alignments of the *S. mikatae*, *S. kudriavzevii*, *S. bayanus*, and *S. paradoxus* genomes, which are the four other sequenced yeast genomes of the yeast sensu stricto clade[1,2]. To examine binding site conservation across the five sensu stricto species, we considered binding site matches two different ways (see Methods). In the first approach, we called a site conserved if the orthologous sequence in all five species was within two standard deviations of the motif average[28] that we determined from the set of regions passing a 0.001 p-value threshold in PBMs. In the second approach, we employed a very strict measure of sequence conservation, in which we required 100% sequence identity at all 9, 9, or 12 nucleotide positions of the TF binding site (for Mig1, Abf1, and Rap1, respectively), in all five species. We found that the level of conservation varied for these three TFs, but that in general for the regions passing the 0.001 Bonferroni-adjusted p-value threshold the binding sites within regions bound in PBMs were just as likely to be conserved as were the binding sites within regions bound in ChIP-chip. Furthermore, the regions bound in PBMs and not in ChIP-chip showed the approximately the same degree of conservation. PBM experiments identified 23, 70, and 38 binding sites for Mig1, Abf1, and Rap1, respectively, that were conserved within two standard deviations in all five species and that were not identified as 'bound' in ChIP-chip experiments[7,8]. Moreover, the regions bound only in PBMs identified many conserved sites that are 100% identical across all five species. Based upon the known conservation level across the sensu stricto genomes[2], the probability of observing even a single binding site that is 100% conserved by chance is extremely small. However, for each TF between six and ten new sites were found that were 100% identical in all five species and bound only in PBMs. Furthermore, this is actually an underestimate of the degree of conservation among TF binding sites because our search was limited to genomic regions that are aligned in all five species and does not consider binding sites that may be conserved in four or fewer species. Thus, we believe that the intergenic regions bound in PBMs are very likely to contain functional in vivo binding sites.

Identification of Target Genes

We examined each of the sets of intergenic regions bound in PBMs to determine whether the candidate target genes, located directly downstream of the bound intergenic regions, were over-represented for particular functional groups of genes[25,26] (see Methods). Among the significantly enriched categories for the target genes derived from the Rap1 PBM data, a large number are consistent with the known regulatory functions of Rap1[29], including the MIPS functional classification categories for ribosome biogenesis ($p<1.0\times10^{-14}$), protein synthesis ($p<1.0\times10^{-14}$), structural constituents of the ribosome ($p<1.0\times10^{-14}$), and cell growth and/or maintenance ($p=3.5\times10^{-12}$). Of note, the Rap1 PBM data identified a greater number of target genes that are annotated members of each of these functional categories than did the combination of the two published ChIP-chip datasets for Rap1. For example, PBM experiments identified eight genes involved in ribosome biogenesis, including two encoding mitochondrial ribosomal proteins, YmL8 and YmL15, whose putative TF binding sites were below the threshold for binding in both published ChIP-chip datasets[7,8]. Consistent with these functions, the deletion strains of the target genes derived from the Rap1 PBM data are enriched for having a slow growth phenotype ($p=1.0\times10^{-4}$). As further support of their functional significance, many of the corresponding enriched target genes from the PBM data had Rap1 sites that were conserved across all five sensu stricto yeast species. Among the newly identified Rap1 putative target genes, 40 were previously uncharacterized, including the ORFs YDR109C, YKL151C, YIL001W, and YKL082C.

Further characterization of these targets may identify heretofore unknown biological functions for Rap1, both expected and unexpected. YDR109C shows strong homology (BLAST E-value=$2.0\times10^{-96}$) to a number of ribulose kinases, and YKL151C shows strong homology (BLAST E-value=$1.0\times10^{-44}$) to a carbohydrate kinase family, suggesting a mechanism by which Rap1 might connect the nutrient status of a cell with its translational capacity. YIL001W shows strong homology (BLAST E-value=$4.0\times10^{-26}$) to human elongation factor 1A binding protein, implying its likely role in protein synthesis. YKL082C, while uncharacterized, is thought to encode a nucleolar protein that is required for normal pre-rRNA processing and is involved in the establishment of cell polarity. Interestingly, gene expression of YKL082C clusters with that of several Rap1 targets identified in PBM and ChIP-chip experiments, including RPS27A (encodes a ribosomal protein), UBP10 (involved in telomeric silencing), as well as BUD22 and BUD27 (bud site selection)[30]. BUD27 is also involved in gene expression controlled by the TOR kinase, which is known for its role in transducing the availability of nutrients into growth and ribosome synthesis. Importantly, all four of the above uncharacterized ORFs are downstream of Rap1 binding sites that are conserved across all five sensu stricto yeast species.

The significantly enriched categories for the target genes derived from the Abf1 PBM data are also consistent with the known regulatory functions of Abf1[29], including the GO biological process categories for cell growth and/or maintenance ($p=1.6\times10^{-7}$), cell organization and biogenesis ($p=8.1\times$ $10^{-6}$), and essentiality (p=$1.2 \times 10^{-4}$). Consistent with these functions, the deletion strains of the target genes derived from the Abf1 PBM data are also enriched for having a slow growth phenotype (p=$5.2 \times 10^{-4}$). Among the Abf1 candidate target gene categories identified in this study that were not previously identified as targets by ChIP-chip analysis, there was an enrichment for the MIPS subcellular localization functional category of the mitochondrial outer membrane (p=$6.8 \times 10^{-4}$), the MIPS protein complex functional category for the mitochondrial translocase complex (p=$6.3 \times 10^{-5}$), and the GO Biological Process functional categories of nucleic acid metabolism (p=$1.1 \times 10^{-5}$) and protein metabolism (p=$1.2 \times 10^{-5}$). While Abf1 is known to be a global regulator, we could not find any prior evidence in the literature for its role in regulating proteins of the mitochondrial membrane or translocase complex. Consistent with these functions, the deletion strains of the target genes derived from the Abf1 PBM data are also enriched for having a slow growth phenotype (p=$5.2 \times 10^{-4}$). In all, we identified 25 novel uncharacterized putative target genes of Abf1 for which ChIP-chip experiments did not show enrichment, approximately half of which are downstream of Abf1 sites conserved across all five sensu stricto species. Of note, YHR020W shows homology (WU-BLAST2 E-value=0.045) to Mst1, a mitochondrial threonine-tRNA synthetase, and to a *Drosophila* glutamyl-prolyl-tRNA synthetase (BLAST E-value=$10^{-172}$). YHR020W previously has been shown to be co-expressed with several other putative Abf1 targets involved in protein and nucleic acid metabolism, including URA7 (pyrimidine biosynthesis), ADE5,7 (purine biosynthesis), and SAM1 (adenosylmethionine synthetase)[30]. Our results suggest that YHR020W is likely to be a true target of Abf1 and to play a role in cellular biogenesis. These observations are consistent with the known regulatory roles of Abf1 in cell growth and maintenance and underscore the ability of PBMs to identify novel, uncharacterized targets of even well-studied TFs.

A much more complete picture of the regulatory functions of Mig1 was possible from analysis of the PBM target genes than could be derived from the ChIP-chip data. Among the enriched functional categories were those for C-compound and carbohydrate metabolism (p=$2.7 \times 10^{-13}$), C-compound, carbohydrate transporters (p=$6.7 \times 10^{-8}$), hexose transport (p=$9.5 \times 10^{-9}$), and alcohol metabolism (p=$2.2 \times 10^{-5}$), all of which are consistent with the known regulatory function of Mig1 as a transcriptional repressor of genes whose products are dispensable in the presence of high levels of glucose[23]. Many of the functional categories and corresponding target genes did not result from analysis of the ChIP-chip data, supporting our hypothesis that the Mig1 ChIP-chip experiments[8] were not performed on cultures grown in ideal conditions for Mig1 to be regulating its target genes. We identified many novel putative target genes for Mig1, 29 of which were previously uncharacterized, including the ORFs YNR071C, YIL024C, YLR089C, YOR356W, and YLR072W.

Further examination of these uncharacterized putative Mig1 targets provided evidence suggestive of their roles in expected pathways and processes. YNR071C shows strong homology (BLAST E-value=$5.3 \times 10^{-89}$) to Gal10, which has a key role in galactose metabolism, making this gene a plausible target for Mig1 repression in the presence of glucose. In addition, YNR071C is up-regulated 6.9-fold in a TOM6 deletion strain[31]; Tom6 is part of a protein complex involved in outer membrane mitochondrial translocation. These results suggest a potential relationship between YNR071C and Tom6 that couples galactose metabolism with aerobic respiration. Another new target, YIL024C, has homology, albeit low (WU-BLAST2 E-value=0.094), to Sip2, a member of a family of proteins that interact with Snf1 and Snf4 and that are involved in the response to glucose starvation[32]. Notably, the predicted Mig1 binding site upstream of YIL024C is conserved (2 SDs position weight matrix (PWM) match) across all five sensu stricto yeast species. Two more novel targets, YLR089C and YOR356W, both encode proteins that are localized to the mitochondria[33] and are likely to be important in the oxidation of fuel molecules. YLR089C shows homology (WU-BLAST2 E-value=$2.6 \times 10^{-6}$) to Bna3, which is involved in NAD biosynthesis, and to alanine aminotransferases in species ranging from plants (BLAST E-value=$10^{-222}$) to human (BLAST E-value=$10^{-116}$). Alanine aminotransferases are pyridoxal enzymes that catalyze the reversible transamination between alanine and 2-oxoglutarate to form pyruvate and glutamate. By mediating the conversion of these four major intermediate metabolites, these transaminases have roles in gluconeogenesis and in amino acid metabolism. YOR356W shows strong homology (BLAST E-value=$10^{-159}$) to a human electron transfer flavoprotein-ubiquinone oxidoreductase. Both YLR089C and YOR356W are immediately downstream of Mig1 binding sites that are 100% identical at all nine positions across all five sensu stricto species. Finally, in addition to the role of Mig1 in regulating carbohydrate and amino acid metabolism, our results also indicate a possible role in cholesterol biosynthesis. Mig1 shows homology (BLAST E-value=$7 \times 10^{-10}$) to the human zinc finger TF WT1, a tumor suppressor gene mutated in Wilms' tumor. WT1 has been implicated in repression of the mevalonate pathway, which is central in cholesterol biosynthesis[34]. Similarly, YLR072W shows homology (WU-BLAST2 E-value=$4.1 \times 10^{-4}$) to Atg26, a sterol 3-beta glucosyl transferase involved in sterol metabolism.

In addition to examining the features of individual putative target genes for each TF, we investigated whether the collective group of target genes showed concerted expression in particular experimental conditions. Because different culture conditions often stimulate different cellular responses and coordinate changes in transcriptional regulation, the success of ChIP-chip experiments hinges on choosing those conditions for which the TF is expressed and active. PBMs, however, are free of this constraint and can identify DNA binding site motifs and putative target genes irrespective of culture conditions. Analysis of these putative target genes can further be used to suggest in vivo conditions for optimal TF activity. Datasets from 643 yeast gene expression microarray experiments performed under various conditions were examined to identify particular conditions in which a significant fraction of PBM target genes were differentially expressed (see Methods). Not surprisingly, the largest fraction of Rap1 targets was up-regulated in conditions optimized for ribosomal biogenesis; e.g., those that confer minimal stress, and those that do not correspond to gene deletions[35]. Furthermore, significant fractions of the Rap1 target genes were down-regulated in a variety of stress response conditions, which are known to involve the repression of ribosomal proteins and protein synthesis[35]. Abf1 target genes show no significant enrichment or deficit in expression in the examined set of conditions, possibly indicating that the optimal conditions for Abf1 binding have not yet been profiled with microarrays. Alternatively, Abf1 target genes may be coregulated by a diverse set of condition-dependent factors, such that no single condition leads to broad correlated expression of the target genes. Mig1 target genes identified by PBM analysis were significantly down-regulated in expression experiments in which the preferred sugars glucose, fructose, and sucrose were the primary carbon sources. This is in agreement with the known role of Mig1 as a repressor of genes involved in alternate carbon source metabolism[23]. Several culture conditions were identified in which Mig1 target genes were up-regulated, despite its role in glucose repression, indicating the absence or inactivation of Mig1. Indeed, many of the most significant conditions (e.g., those in which a significant fraction of PBM target genes were differentially expressed) involved stationary phase cultures; stationary phase onset has been associated with derepression by Mig1[36]. Taken together, these results show that in conjunction with expression profiling, PBM analysis has the potential to provide insight into the functions of particular TFs and to identify conditions in which they are active in vivo.

This PBM technology allows rapid, high-throughput characterization of the DNA binding site sequence specificities of TFs in a single day, and thus can connect TFs to the genes they regulate. In addition to identifying enriched functional categories of known and newly discovered target genes, we also identified many uncharacterized ORFs as candidate target genes of Rap1, Abf1, and Mig1. Moreover, the Mig1 data highlight one scenario in which PBM data may be particularly valuable; e.g., ChIP-chip experiments require that the cells be maintained in culture conditions in which the TF of interest is expressed and nuclear. As could be seen for Mig1, PBM experiments will be particularly useful when ChIP-chip experiments do not result in enough enrichment of bound fragments in the immunoprecipitated sample to permit identification of the DNA sites bound in vivo. Moreover, integrating an epitope tag on the genomic copy of the TF, which allowed the use of a single antibody in the 106 ChIP-chip experiments performed by Lee et al.[8], is not as trivial in many other organisms as it is in yeast; instead in general one has to rely upon protein-specific antibodies that are both specific and successful in chromatin immunoprecipitation, and the generation of such antibodies is not a trivial undertaking.

It is possible that the PBM and ChIP-chip binding site motifs will not correspond so closely for all proteins. Such differences may help us to identify either whether there are significant in vivo effects due to either chromatin structure or cofactors important for sequence-specific binding. Even though the DNA in PBM experiments is not in the same state as it might be if it were to be bound by the TF in vivo, results from PBM experiments can provide valuable data on the sequence specificity of TFs, particularly those which have been poorly understood or uncharacterized thus far. Performing ChIP-chip experiments on yeast grown under a variety of different culture conditions will help to confirm our predictions that particular sets of newly identified binding sites are indeed bound in vivo. Furthermore, the combination of PBM data with mRNA expression data[3,4], ChIP-chip[5-8], protein-protein interaction data[9,10,12], and prior genetic and biochemical data in the literature will contribute towards more detailed models of and a more thorough understanding of gene regulatory networks in yeast[37].

The data presented here indicate that the PBM approach works for TFs with DNA binding domains of a number of different structural classes, including those whose binding induces DNA bending[21]. Since PBM experiments are highly scalable, they could readily be adapted for the analysis of all possible DNA sequence variants. Similarly, there are hundreds of predicted DNA binding proteins in yeast and thousands of predicted TFs in other genomes that could be screened for sequence-specific binding by PBM experiments. For example, a microarray consisting of roughly 30,000 spots of 1 kb sequence, enriched for the portions of the *Drosophila melanogaster* or human genome likely to contain regulatory elements, could be examined by PBMs to characterize the DNA binding specificities of over 670 *D. melanogaster* TFs[38] or of the ~2000 human TFs[39,40]. Since dozens of PBM experiments could be performed in parallel in a single day, this technology provides significant cost and time advantages over other methods, which can take months to measure the effects of mutations for a large set of variant DNA-protein interactions.

The effects of different concentrations of TFs as well as of protein cofactors, protein modifications, small molecule cofactors such as metabolites, or various binding conditions could be measured with PBMs. PBMs could be used to distinguish the relative binding preferences of various whole or partially fractionated cell lysates, such as from various cell types, sampled at different time points or grown under different conditions.

Bioinformatic analysis of PBM will provide more informative data than a mononucleotide PWM, as it has been shown previously that nucleotides of TF binding sites frequently do not act independently in binding by TFs[15-17,41]. Moreover, as more PBM experiments are performed, the vast datasets that would be generated on DNA-protein interactions could yield the necessary data required to determine what predictive rules may exist that describe DNA recognition by sequence-specific TFs[42].

Methods

Synthesis of DNA Microarrays

Microarrays spotted with double-stranded DNAs containing either positive or negative control binding sites for Rpn4 for the PBM proof-of-principle experiments with CBP-FLAG-Rpn4 were synthesized essentially as described previously[14]. Whole-genome yeast intergenic microarrays were synthesized essentially as described previously[5].

Expression and Purification of Yeast Transcription Factors

N-terminal CBP-FLAG fusions of RPN4 were created by cloning RPN4 into the pCAL-n-FLAG™ vector (Stratagene). The resulting CBP-FLAG-RPN4 fusion constructs were full-length sequence-verified to ensure that no mutations had been introduced during cloning. Verified CBP-FLAG-RPN4 constructs were transformed into BL21-GOLD™ (DE3)pLysS *E. coli* (Stratagene) and expressed by inoculating LB medium containing 50 µM zinc acetate and 50 µg/ml carbemicillin with an overnight culture (1:20 dilution), growing at 30° C. to an $OD_{600}$ between 0.3 and 0.5, and then inducing with 1 mM IPTG until an $OD_{600}$ of 1.6 was reached. Cell pellets were stored at −80° C., and subsequently were thawed on ice and lysed with CELLYTICB™ Bacterial Cell Lysis Extraction Reagent (Sigma) containing 50 µM zinc acetate. The CBP-FLAG fusion proteins were purified with anti-FLAG M2 affinity gel (Sigma), and subsequently quantified. Sequence-specific binding of the purified Rpn4 fusion protein was verified with EMSAs using probes containing the consensus PACE site[26]. Purified proteins were stored at −80° C. until use.

N-terminal GST-$His_6$ fusions of Rap1, Abf1, and Mig1 were produced essentially as described previously[11]. Briefly, the fusion proteins were expressed in *S. cerevisiae*, and then individually purified with glutathione beads (Amersham), concentrated using Microcon YM-30™ filters (Millipore), and subsequently quantified. Purified proteins were stored at −80° C. until use.

Protein Binding Microarray (PBM) Experiments

PBM experiments and SYBRGREEN™ staining of the DNA microarrays were performed in triplicate, essentially as described previously[14]. Briefly, previously purified proteins were thawed on ice and diluted to a 20 nM final concentration in a protein binding reaction mixture consisting of PBS, 50 µM zinc acetate (ZnAc), 2% (w/v) nonfat dried milk, 0.3 ng/µl salmon testes DNA (Sigma), and 0.2 µg/µl BSA; this protein binding reaction was allowed to pre-incubate for 1 hr at room temperature. Microarrays were pre-wet in PBS/0.01% Triton-X-100 and then blocked with 2% milk in PBS for 1 hr. The blocked microarrays were washed once with PBS/0.1% Tween 20, and then once with PBS/50 µM ZnAc/0.01% Triton X-100 (PBS/ZnAc/TX100). The pre-incubated protein binding mixtures were then applied to the microarrays and binding was allowed to proceed for 1 hr. The microarrays then were washed once with PBS/ZnAc/0.5% Tween 20, and then once with PBS/ZnAc/TX100. Alexa 488-conjugated rabbit anti(GST) polyclonal antibody (Molecular Probes) or Cy3-conjugated mouse anti(FLAG) M2 monoclonal antibody (Sigma) was diluted in PBS/ZnAc containing 2% milk, pre-incubated for at least 30 min, and applied to the microarray. After incubation for 1 hr, the microarrays were washed 3 times with PBS/ZnAc/0.05% Tween 20, and once with PBS/ZnAc. The slides were then spun dry, and stored in a closed box until being scanned.

Microarray Imaging and Data Analysis

All whole-genome yeast intergenic microarrays were from the same print run, so as to minimize variation. We typically scanned (GSI Lumonics SCANARRAY™ 4000 or SCANARRAY™ 5000) the labeled, protein-bound microarrays and the SYBRGREEN™ I stained microarrays at 3-6 different laser power intensities or PMT gain settings per microarray; this allowed us to capture signal intensities for even very low signal intensity spots, while ensuring that we captured sub-saturation signal intensities for each of the spots on the microarray[14]. Microarrays were scanned using appropriate lasers and filter sets, essentially as described previously[14].

Microarray TIF images were quantified using GenePix Pro version 3.0 software (Axon Instruments, Inc.). Specifically, background-subtracted median intensities were calculated using the median local background. We used MASLINER™ (MicroArray Spot LINEar Regression) software to calculate the relative signal intensities over the full series of laser power (or PMT gain) setting scans in a semi-automated fashion. Specifically, masliner combines the linear ranges of multiple scans from different scanner sensitivity settings onto an extended linear scale[14,43]. This resulted in the dynamic range of the final PBM and SYBRGREEN™ I stained microarrays to have fluorescence intensities that spanned 5 to 6 orders of magnitude.

The resulting microarray data were filtered with a number of quality control criteria so that only data from high quality spots were retained. First, for each of the triplicate microarrays, we removed data corresponding to any flagged spots (e.g., spots that had dust flecks, etc.). Data from each of three triplicate microarrays were normalized according to total signal intensity, so that the average spot intensity was the same for all three slides. Then, within each individual slide, the data were separated into sectors, according to their local region on the slide; for the whole-genome yeast intergenic arrays we sectored the spots into the 32 subgrids of the printed microarray. The data were then normalized again so that the mean spot intensity was the same over all the sectors; this served to normalize for any region-specific inhomogeneities in the background and also binding and labeling reactions. Any spots with SD/median greater than 2, e.g., spots with highly variable pixel signal intensities, were filtered out. The background-subtracted, normalized signal intensities for all spots with reliable data in at least two of the three replicate microarrays were averaged, and the SD/mean was calculated. The SYBRGREEN™ I microarray data were treated exactly the same way, except that any spots with fewer than 50% pixels with signal intensities greater than two standard deviations beyond the median background signal intensity were also filtered out, as these spots presumably do not have enough DNA present to allow accurate quantification of signal intensities. For the Rap1, Abf1, and Mig1 PBM datasets, ~91-96% of 6723 unique spots passed these criteria.

We calculated the fractional signal intensity of each spot, relative to the total signal intensity on the microarray. We then calculated the $\log_2$ ratio of the mean PBM signal intensity divided by the mean SYBRGREEN™ I signal intensity, and created a scatter plot of the log ratio versus the spots' SYBRGREEN™ I signal intensities. Although we expect that the log ratio should be independent of DNA concentration, we have found that higher DNA concentrations, as determined by higher SYBRGREEN™ I signal intensities, appear to bind proportionately less protein. In order to restore the independence of log ratio and SYBRGREEN™ I intensity, the scatter plot was fit with a locally weighted least squares regression using the LOWESS function[44] of the R statistics package[45] (smoothing parameter=0.5). We subtracted the value of the regression at each spot from its log ratio, yielding a modified log ratio that is independent of DNA concentration. We then plotted the distribution of all log ratios as a histogram (bin size=0.05), which for Rap1, Abf1, and Mig1 resembled a Gaussian distribution with a heavy tail. We determined the mode of the distribution by searching for the window of nine bins with the highest number of spots and taking the middle bin. We then reflected all values less than the mode and fit these values to a Gaussian function using the MATHEMATICA™ software package (Wolfram Research, Inc.). This gave the mean and standard deviation of the distribution, and the mean was used to adjust the log ratios so that the peak was centered on zero. We calculated a p-value for each individual spot based on the magnitude of its log ratio relative to the standard deviation of the Gaussian distribution, using the normal error integral. In order to correct for multiple hypothesis testing, all individual p-values were adjusted to a modified significance level using the Modified Bonferroni Method[15,46]. For significance testing of the PBM data, we used an initial a=0.001, which corresponded to a' equal to approximately $1.5 \times 10^{-7}$ for the highest-ranking test case, as we were typically evaluating ~6400 unique spots.

DNA Motif Finding and Group Specificity Score

For analysis of sequences for over-represented DNA sequence motifs, we used BIOPROSPECTOR™[24]. We chose BIOPROSPECTOR™ over other available motif finding programs because it proved to be the most inclusive in accepting the largest number of input sequences in construction of the TF binding site motifs. To search for motifs that were over-represented in PBM experiments, we used all sequences from spots that had a Bonferroni-corrected p-value less than or equal to 0.001 as input. To search for motifs that were over-represented in the intergenic regions bound in ChIP-chip experiments, we input either all sequences with a p-value less than or equal to 0.001[8] or all sequences with a median percentile rank at or above 0.92 in the six replicate experiments and below 0.92 in controls[7]. For each set of input sequences, we performed separate searches at each width between 6 and 18 nucleotides in order to identify the highest scoring motifs at each width. We chose the single motif with the highest group specificity score[26] to be the most significant, using the set of all sequences spotted on the microarray as the background. Briefly, the group specificity score indicates the degree to which the property of containing the sequence motif is specific to the input set of intergenic regions, as determined from the most significantly bound spots on the microarrays, with a smaller group specificity score indicating that the motif is more specific to the input set of spots (e.g., either the spots beyond a 0.001 p-value threshold in either the PBM or Lee et al.[8] ChIP-chip data, or the spots at or beyond the $92^{nd}$ percentile rank in the Lieb et al.[7] ChIP-chip data, or the randomly selected spots in the computational random controls). In order to assess the statistical significance of the DNA sequence motifs resulting from analysis of the PBM experiments, we performed a set of computational negative control experiments. In these computational negative controls, we performed identical motif searches on 10 individual sets of randomly selected spots from the yeast intergenic microarrays for each TF, with each random set containing the same number of sequences as the original input sets for each of the Rap1, Abf1, and Mig1 PBM datasets. The range of group specificity scores for the Rap1 control sets was $2.2\times10^{-5}$ to $3.5\times10^{-11}$, with a geometric mean equal to $8.4\times10^{-8}$; the range of group specificity scores for the Abf1 control sets was $5.6\times10^{-3}$ to $1.3\times10^{-6}$, with a geometric mean equal to $3.7\times10^{-5}$; and the range of group specificity scores for the Mig1 control sets was $4.8\times10^{-3}$ to $1.8\times10^{-5}$, with a geometric mean equal to $4.8\times10^{4}$. Thus, the Rap1, Abf1, and Mig1 motifs identified from the intergenic regions identified as bound in PBM experiments had highly significant group specificity scores as compared to the random controls. We also determined the motifs' Pearson correlation coefficients using CompareACE[26]. The correlation coefficients were as follows: Rap1 PBM versus Lee et al.[8] ChIP-chip: 0.992; Rap1 PBM versus Lieb et al.[7] ChIP-chip: 0.995; Rap1 PBM versus TRANSFAC: 0.953; Rap1 Lee et al.[8] versus Lieb et al.[7] ChIP-chip: 0.985; Rap1 Lee et al.[8] ChIP-chip versus TRANSFAC: 0.921; Rap1 Lieb et al.[7] ChIP-chip versus TRANSFAC: 0.950; Abf1 PBM versus ChIP-chip[8]: 0.989; Abf1 PBM versus TRANSFAC: 0.978; Abf1 ChIP-chip[8] versus TRANSFAC: 0.986; Mig1 PBM versus ChIP-chip[8]: 0.453; Mig1 PBM versus TRANSFAC: 0.938; Mig1 ChIP-chip[8] versus TRANSFAC: 0.406.

Electrophoretic Mobility Shift Assays (EMSAs)

EMSAs were performed according to manufacturer's protocols for the LIGHTSHIFT® Chemiluminescent EMSA Kit (Pierce). Complementary biotinylated DNA oligonucleotides, each 45 by in length, were synthesized (Integrated DNA Technologies) such that they contained the predicted Rap1 binding site, flanked by its native sequence from the given intergenic region. A positive control probe containing a known Rap1 binding site and a negative control probe lacking a Rap1 binding site were also synthesized and used in EMSAs.

Analysis of Functional Category Enrichment

Analysis of a group of genes for enrichment for a particular functional annotation previously has been used to analyze sets of yeast genes that comprise particular gene expression clusters[25]. We used the web-based tool FunSpec for the statistical evaluation of the groups of genes downstream of the 'bound' intergenic regions, for groups of over-represented gene and protein categories with respect to existing functional category information from a number of public and published databases[47]. Like the group specificity score described above[25,26], FunSpec uses the hypergeometric distribution to calculate a p-value for functional category enrichment[25,26].

Analysis of Cross-Species Sequence Conservation

We searched for conserved putative binding sites in the five sequenced genomes of the yeast sensu stricto clade: *S. cerevisiae*, *S. mikatae*, *S. kudriavzevii*, *S. bayanus*, and *S. paradoxus*. Our searches were limited to the aligned regions in the MULTIZ™ multiple sequence alignment. Regions aligned between *S. cerevisiae* and each of the other four species were separately mapped onto the *S. cerevisiae* chromosomal coordinates. We used ScanACE[26] to search all five genomes for sequence matches within two standard deviations of the motif identified from PBM experiments. In our first approach, a site was called conserved if its ScanACE score was within two standard deviations of the motif average[28] that we determined from the set of regions passing a 0.001 p-value threshold in PBMs and if its relative position in each genome differed by no more than 15 bp. In our second approach, a site was called exactly conserved if it satisfied the previous conditions and was identical in all five species at each of the informative positions. Here, for "exact" conservation we employed a very strict measure of sequence conservation, in which we required 100% sequence identity at all informative nucleotide positions of the binding site (9, 9, or 12 positions for Mig1, Abf1, and Rap1, respectively), in all five species. We defined informative positions to be those with an information content of greater than 0.5 bits in the PBM-derived motif. Analyses were performed with Perl scripts written by M.F.B.

Analysis of Correlation of Target Genes with Gene Expression Data

Gene expression data from 643 yeast expression microarray experiments across a variety of culture conditions[48] were normalized so that the fold-change within each microarray had a mean of 0 and standard deviation of 1. In order to identify conditions under which a particular TF either activated or failed to repress transcription, we calculated the fraction of putative target ORFs with at least a 2.5-fold increase in gene expression for each individual condition. Similarly, to find conditions in which a TF acted as a repressor or failed to activate transcription, we calculated the fraction of putative target ORFs with at least a 2.5-fold decrease in gene expression for each condition. Significance was assessed by comparison with 100 sets of randomized ORFs, matched in size to the lists of target genes for each TF.

References

1. Kellis, M., Patterson, N., Endrizzi, M., Birren, B. & Lander, E. Sequencing and comparison of yeast species to identify genes and regulatory elements. Nature 423, 241-254 (2003).

2. Cliften, P. et al. Finding functional features in *Saccharomyces* genomes by phylogenetic footprinting. Science 301, 71-76 (2003).

3. Wodicka, L., Dong, H., Mittmann, M., Ho, M. H. & Lockhart, D. J. Genome-wide expression monitoring in *Saccharomyces cerevisiae*. Nat. Biotechnol. 15, 1359-1367 (1997).

4. DeRisi, J. L., Iyer, V. R. & Brown, P. O. Exploring the metabolic and genetic control of gene expression on a genomic scale. Science 278, 680-686 (1997).

5. Ren, B. et al. Genome-wide location and function of DNA binding proteins. Science 290, 2306-2309 (2000).

6. Iyer, V. R. et al. Genomic binding sites of the yeast cell-cycle transcription factors SBF and MBF. Nature 409, 533-538 (2001).

7. Lieb, J. D., Liu, X., Botstein, D. & Brown, P. O. Promoter-specific binding of Rap1 revealed by genome-wide maps of protein-DNA association. Nat. Genet. 28, 327-334 (2001).

8. Lee, T. et al. Transcriptional regulatory networks in *Saccharomyces cerevisiae*. Science 298, 799-804 (2002).

9. Ito, T. et al. Toward a protein-protein interaction map of the budding yeast: A comprehensive system to examine two-hybrid interactions in all possible combinations between the yeast proteins. Proc. Natl. Acad. Sci. USA 97, 1143-1147 (2000).

10. Uetz, P. et al. A comprehensive analysis of protein-protein interactions in *Saccharomyces cerevisiae*. Nature 403, 623-627 (2000).

11. Zhu, H. et al. Global analysis of protein activities using proteome chips. Science 26, 2101-2105 (2001).

12. Ho, Y. et al. Systematic identification of protein complexes in *Saccharomyces cerevisiae* by mass spectrometry. Nature 415, 180-183 (2002).

13. Oliphant, A. R., Brandi, C. J. & Struhl, K. Defining the sequence specificity of DNA-binding proteins by selecting binding sites from random-sequence oligonucleotides: analysis of yeast GCN4 protein. Mol. Cell. Biol. 9, 2944-2949 (1989).

14. Bulyk, M. L., Huang, X., Choo, Y. & Church, G. M. Exploring the DNA-binding specificities of zinc fingers with DNA microarrays. Proc. Natl. Acad. Sci. USA 98, 7158-7163 (2001).

15. Bulyk, M., Johnson, P. & Church, G. Nucleotides of transcription factor binding sites exert interdependent effects on the binding affinities of transcription factors. Nucleic Acids Res. 30, 1255-1261 (2002).

16. Benos, P., Bulyk, M. & Stormo, G. Additivity in protein-DNA interactions: how good an approximation is it? Nucleic Acids Res. 30, 4442-4451 (2002).

17. Lee, M.-L., Bulyk, M., Whitmore, G. & Church, G. A statistical model for investigating binding probabilities of DNA nucleotide sequences using microarrays. Biometrics 58, 981-988 (2002).

18. Udalova, I., Mott, R., Field, D. & Kwiatkowski, D. Quantitative prediction of NF-kappa B DNA-protein interactions. Proc. Natl. Acad. Sci. USA 99, 8167-8172 (2002).

19. Schena, M., Shalon, D., Davis, R. W. & Brown, P. O. Quantitative monitoring of gene expression patterns with a complementary DNA microarray. Science 270, 467-470 (1995).

20. Diffley, J. & Stillman, B. Purification of a yeast protein that binds to origins of DNA replication and a transcriptional silencer. Proc. Natl. Acad. Sci. USA 85, 2120-2124 (1988).

21. McBroom, L. D. & Sadowski, P. D. DNA bending by *Saccharomyces cerevisiae* ABF1 and its proteolytic fragments. J. Biol. Chem. 269, 16461-16468 (1994).

22. Konig, P., Giraldo, R., Chapman, L. & Rhodes, D. The crystal structure of the DNA-binding domain of yeast RAP1 in complex with telomeric DNA. Cell 85, 125-136 (1996).

23. Lutfiyya, L. L. et al. Characterization of three related glucose repressors and genes they regulate in *Saccharomyces cerevisiae*. Genetics 150, 1377-1391 (1998).

24. Liu, X., Brutlag, D. & Liu, J. BioProspector: discovering conserved DNA motifs in upstream regulatory regions of co-expressed genes. Pac. Symp. Biocomput., 127-138 (2001).

25. Tavazoie, S., Hughes, J., Campbell, M., Cho, R. & Church, G. Systematic determination of genetic network architecture. Nat. Genet. 22, 281-285 (1999).

26. Hughes, J. D., Estep, P. W., Tavazoie, S. & Church, G. M. Computational identification of cis-regulatory elements associated with groups of functionally related genes in *Saccharomyces cerevisiae*. J. Mol. Biol. 296, 1205-1214 (2000).

27. Wingender, E. et al. TRANSFAC: an integrated system for gene expression regulation. Nucleic Acids Res. 28, 316-319 (2000).

28. Robison, K., McGuire, A. M. & Church, G. M. A comprehensive library of DNA-binding site matrices for 55 proteins applied to the complete Escherichia coli K-12 genome. J. Mol. Biol. 284, 241-254 (1998).

29. Planta, R. J. Regulation of ribosome synthesis in yeast. Yeast 13, 1505-18 (1997).

30. Beer, M. A. & Tavazoie, S. Predicting gene expression from sequence. Cell 117, 185-98 (2004).

31. Hughes, T. R. et al. Functional discovery via a compendium of expression profiles. Cell 102, 109-26 (2000).

32. Jiang, R. & Carlson, M. The Snf1 protein kinase and its activating subunit, Snf4, interact with distinct domains of the Sip1/Sip2/Ga183 component in the kinase complex. Mol. Cell. Biol. 17, 2099-106 (1997).

33. Palecek, S. P., Parikh, A. S., Huh, J. H. & Kron, S. J. Depression of *Saccharomyces cerevisiae* invasive growth on non-glucose carbon sources requires the Snf1 kinase. Mol. Microbiol. 45, 453-69 (2002).

34. Rae, F.K. et al. Analysis of complementary expression profiles following WT1 induction versus repression reveals the cholesterol/fatty acid synthetic pathways as a possible major target of WT1. Oncogene 23, 3067-79 (2004).

35. Gasch, A. P. et al. Genomic expression programs in the response of yeast cells to environmental changes. Mol Biol Cell 11, 4241-57 (2000).

36. Unnikrishnan, I., Miller, S., Meinke, M. & LaPorte, D. C. Multiple positive and negative elements involved in the regulation of expression of GSY1 in *Saccharomyces cerevisiae*. J Biol Chem 278, 26450-7 (2003).

37. Hartemink, A., Gifford, D., Jaakkola, T. & Young, R. Combining location and expression data for principled discovery of genetic regulatory network models. Pac. Symp. Biocomput., 437-449 (2002).

38. Adams, M. et al. The genome sequence of Drosophila melanogaster. Science 287, 2185-2195 (2000).

39. Venter, J. C. et al. The sequence of the human genome. Science 291, 1304-1351 (2001).

40. Lander, E. S. et al. Initial sequencing and analysis of the human genome. Nature 409, 860-921 (2001).

41. Man, T. K. & Stormo, G. D. Non-independence of Mnt repressor-operator interaction determined by a new quantitative multiple fluorescence relative affinity (QuMFRA) assay. Nucleic Acids Res. 29, 2471-2478 (2001).

42. Desjarlais, J. R. & Berg, J. M. Toward rules relating zinc finger protein sequences and DNA binding site preferences. Proc. Natl. Acad. Sci. USA 89, 7345-7349 (1992).

43. Dudley, A., Aach, J., Steffen, M. & Church, G. Measuring absolute expression with microarrays with a calibrated reference sample and an extended signal intensity range. Proc. Natl. Acad. Sci. USA 99, 7554-7559 (2002).

44. Cleveland, W. & Devlin, S. Locally weighted regression: An approach to regression analysis by local fitting. J. American Statistical Association 83, 596-610 (1988).

45. Ihaka, R. & Gentleman, R. R: A language for data analysis and graphics. J. Computational and Graphical Statistics 5, 299-314 (1996).

46. Sokal, R. & Rohlf, R. Biometry: The Principles and Practice of Statistics in Biological Research, (W. H. Freeman and Company, New York, 1995).

47. Robinson, M., Grigull, J., Mohammad, N. & Hughes, T. FunSpec: a web-based cluster interpreter for yeast. BMC Bioinformatics 3, 35 (2002).

48. Stuart, J. M., Segal, E., Koller, D. & Kim, S. K. A gene-coexpression network for global discovery of conserved genetic modules. Science 302, 249-55 (2003).

49. Schneider, T. D. & Stephens, R. M. Sequence logos: a new way to display consensus sequences. Nucleic Acids Res. 18, 6097-100 (1990).

A number of embodiments of the invention have been described. Nevertheless, it will be understood that various modifications may be made without departing from the spirit and scope of the invention. Accordingly, other embodiments are within the scope of the following claims.

What is claimed is:

1. A nucleic acid array comprising a plurality of addresses, each address of the plurality comprising a synthetic nucleic acid molecule wherein:
   (i) the array comprises synthetic nucleic acid molecules, the molecules collectively providing at least 80% of all possible sites of length k, k being greater than 5;
   (ii) each nucleic acid molecule is associated with an address of the plurality and has a length greater than 6 nucleotides and less than 150 nucleotides; and
   (iii) the array has fewer addresses than 0.5 times the number of all possible sites of length k.

2. The array of claim 1, wherein the nucleic acid molecules collectively provide at least 98% of all possible sites of length k, and the array has fewer addresses than 0.5 times 98% of the number of all possible sites of length k.

3. The array of claim 2, wherein the nucleic acid molecules collectively provide all possible sites of length k, and the array has fewer addresses than 0.5 times 80% of the number of all possible sites of length k.

4. The array of claim 1, wherein k is between 7 and 10.

5. The array of claim 1, wherein each of the sites of length k is represented at least twice, each time in a different context.

6. The array of claim 1, wherein the array comprises a planar substrate.

7. The array of claim 1, wherein the nucleic acid molecules are double-stranded DNAs.

8. A method of evaluating interaction specificity of a test compound, the method comprising: contacting the test compound to the array of any one of claim 1-5, 6 or 7, and evaluating interactions between the test compound and one or a subset of nucleic acid molecules of the array.

9. The method of claim 8, wherein the test compound is in solution prior to the contacting, and the step of evaluating comprises detecting the test compound on the array.

* * * * *

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
tcaagtcaat cggtcc                                                    16

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
atcgcagtta gcaatg                                                    16

<210> SEQ ID NO 3
<211> LENGTH: 16
<212> TYPE: DNA
<213> ORGANISM: Artificial Sequence
<220> FEATURE:
<223> OTHER INFORMATION: Primer

<400> SEQUENCE: 3
gggtagaggg tttcaa                                                    16
```